(12) United States Patent
Turner et al.

(10) Patent No.: US 6,307,099 B1
(45) Date of Patent: Oct. 23, 2001

(54) PRODUCTION OF TEREPHTHALIC ACID

(75) Inventors: John Arthur Turner, North Yorkshire; David John Royall; Duncan Stuart Hugall, both of Cleveland; Graham Howard Jones, North Yorkshire; Duncan Charles Woodcock, Cheshire, all of (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/380,039

(22) PCT Filed: Feb. 19, 1998

(86) PCT No.: PCT/GB98/00528
§ 371 Date: Jan. 7, 2000
§ 102(e) Date: Jan. 7, 2000

(87) PCT Pub. No.: WO98/38150
PCT Pub. Date: Sep. 3, 1998

Related U.S. Application Data
(60) Provisional application No. 60/039,662, filed on Feb. 28, 1997.

(30) Foreign Application Priority Data

Feb. 27, 1997 (GB) .................................................. 9703897

(51) Int. Cl.$^7$ ........................................................ C07C 51/16
(52) U.S. Cl. .................................................................. 562/412
(58) Field of Search ............................................. 562/412

(56) References Cited

U.S. PATENT DOCUMENTS

| 3,507,913 | 4/1970 | Mato et al. . |
| 3,665,033 | 5/1972 | Ohlswager et al. . |
| 4,892,970 | 1/1990 | Nowicki et al. . |

FOREIGN PATENT DOCUMENTS

| 041 784 | 12/1981 | (EP) . |
| 1 574 651 | 9/1980 | (GB) . |

*Primary Examiner*—Paul J. Killos
(74) *Attorney, Agent, or Firm*—Charles E. Krukiel

(57) ABSTRACT

An aromatic carboxylic acid such as terephthalic acid is produced by the liquid phase oxidation of a precursor thereof, the oxidation being carried out in such a way that substantially all of the aromatic carboxylic acid produced in the course of the reaction is maintained in solution during the reaction.

5 Claims, 9 Drawing Sheets

PRODUCTION OF TEREPHTHALIC ACID

This application claims benefit of provisional application Ser. No. 60/039,662 filed Feb. 28, 1997.

This invention relates to the production of aromatic carboxylic acids which are sparingly soluble in acetic acid and water, particularly terephthalic acid.

Terephthalic acid is an important intermediate for the production of polyester polymers which are used typically for fibre production and in the manufacture of bottles. Current state-of-the-art technology for the manufacture of terephthalic acid involves the liquid phase oxidation of paraxylene feedstock using molecular oxygen in a solvent comprising lower C2 to C6 aliphatic monocarboxylic acid, usually acetic acid, in the presence of a dissolved heavy metal catalyst system incorporating a promoter such as bromine. The reaction is carried out in at least one stirred vessel under elevated temperature and pressure conditions, typically 150 to 250° C. and 6 to 30 bara respectively, with air being sparged into the reaction mixture and typically produces terephthalic acid in high yield, e.g. at least 95%. Isothermal reaction conditions are maintained in the oxidation vessel by allowing evaporation of the solvent, together with water produced in the reaction, the resulting vapour being condensed and returned to the reactor vessel as reflux. In the conventional production of terephthalic acid, because terephthalic acid is only sparingly soluble in the solvent, a substantial proportion the product precipitates in the course of the reaction and as a result impurities such as 4-carboxybenzaldehyde (4-CBA) and colour bodies co-precipitate with the terephthalic acid to produce a crude product which, to meet the requirements of many polyester producers, has to be purified to reduce its impurity content. In one purification process, the crude product is dissolved in water and, under elevated temperature and pressure conditions, is contacted with hydrogen in the presence of a hydrogenation catalyst, the purified terephthalic acid thereafter being recovered by crystallisation and solids-liquid separation techniques.

The present invention seeks to provide a process for the production of terephthalic acid in such a way as to afford scope for achieving a sufficiently pure product for subsequent use without necessarily having to carry out an additional purification process.

According to a first aspect of the present invention there is provided a process for the production of terephthalic acid by the liquid phase oxidation of a precursor of terephthalic acid with oxygen in a reaction medium containing the precursor and a solvent under conditions such that substantially all of the terephthalic acid produced in the oxidation reaction zone is maintained in solution during the reaction, characterised in that the oxidation reaction is carried out by passing the reaction medium through the reaction zone in a continuous plug flow reaction regime.

Preferably the reactor is a plug flow reactor or a series of two or more plug flow reactors, preferably operated in a non-boiling mode, although the various aspects of the invention defined herein are not limited to this particular type of continuous flow reactor. For instance, the reaction may be carried out in a series of non-boiling continuous stirred tank reactors so as to approximate a continuous plug flow regime or in a reaction system comprising one-or more non-boiling continuous stirred tank reactors and one or more plug flow reactors arranged in any sequence.

By "continuous plug flow regime" we mean a reactor in which reactants are introduced and products withdrawn simultaneously in a continuous manner, as opposed to a batch-type reactor. The residence time of the reaction medium within the reaction zone is generally no more than 10 minutes and is preferably no more than 8 minutes, with residence times of 5 minutes or less, e.g. 3 minutes or less, being achievable.

According to a second aspect of the present invention, which may be but is not necessarily used in conjunction with the first aspect of the invention, there is provided a process for the production of terephthalic acid by the liquid phase oxidation of a precursor of terephthalic acid with oxygen in a reaction medium containing the precursor and a solvent under conditions such that substantially all of the terephthalic acid produced in the oxidation reaction zone is maintained in solution during the reaction, characterised in that the oxidation reaction is carried out with substantially all of the oxygen dissolved in the reaction medium.

Thus, in this aspect of the present invention, the liquid phase oxidation reaction is carried out in such a way as to maintain substantially all of the resulting terephthalic acid in solution during the reaction thereby reducing the extent to which the main impurity, 4-CBA, contaminates the recovered terephthalic acid as a result of co-precipitation during the reaction. Substantially all of the oxygen utilised in the process according to this aspect of the present invention is dissolved in the reaction medium. The use of dissolved oxygen in the reaction medium allows the oxygen to be more uniformly distributed throughout the reaction medium. In this manner, oxygen starved regions within the reaction medium can be minimised with consequential reduction in the formation of undesirable reaction by-products such as trimellitic acid, benzoic acid and colour bodies. Overall, this leads to the possibility of producing product with a low level of contamination and without undue solvent burning which, in turn, allows elimination of the purification process conventionally employed in the production of terephthalic acid of sufficient quality for use in high grade polyester manufacture.

Although in the above aspect and other aspects of the invention disclosed herein, it is preferred that all of the terephthalic acid produced in the reaction is maintained in solution during the reaction, we do not exclude the possibility of some precipitation during the reaction, e.g. up to 10%, more usually no more than 5% but desirably no more than about 2% by weight of the terephthalic acid produced may precipitate during the course of the reaction.

Preferably the reaction medium is produced by combining at least two separate liquid phase components and at least part of the oxygen is added to and dissolved in one or more of said liquid phase components before such components are combined to form the reaction medium.

For instance, the separate liquid phase components may include one component consisting of or containing said precursor and a second component consisting of or containing said solvent and at least part of the oxygen required for the reaction may be added to and dissolved in the second component so that reaction between the oxygen and the precursor cannot commence until the components are combined to form the reaction medium.

Usually the solvent is predominantly an aliphatic monocarboxylic acid (preferably containing 2 to 6 carbon atoms) and may for instance be selected from acetic acid, propionic acid, butyric acid, isobutyric acid, n-valeric acid, trimethylacetic acid, caprioic acid and mixtures of one of these carboxylic acids with water, which in any event is produced in the course of the reaction. The presently preferred solvent is acetic acid and water. However, we do not preclude the possibility of using other solvents such as benzoic acid, e.g. a mixture of benzoic acid and water.

The water content used in the conventional production of terephthalic acid by liquid phase oxidation of paraxylene is typically such that water comprises between 3 and 10% by weight of the combined solvent-forming carboxylic acid/water supplied to the reaction zone. A feature applicable to the various aspects of the invention disclosed herein is that the water content can be substantially greater than that present in the the total feed to the reaction zone of a conventional terephthalic acid production process; in the various aspects of the invention disclosed herein the reaction medium composition at the time of commencement of the reaction may contain water in an amount of ranging from about 3% up to about 30%, e.g. 12%, or greater (e.g. from 10% up to 30%) by weight. The increased water content becomes feasible because of the relatively high solvent to precursor ratio employed in the process of the invention in order to ensure that substantially all of the terephthalic acid produced remains in solution during the reaction. For example, where the precursor comprises paraxylene, the solubility of paraxylene in an acetic acid/water mixture falls sharply with increasing water content and this imposes constraints on the amount of water that can be present in the reaction medium in conventional terephthalic acid production since the solvent/paraxylene ratios are low, typically between 4:1 and 7:1. Thus, in the process of the present invention, increased water content may be tolerable.

The solvent/precursor ratio is usually at least 30:1, e.g. at least 50:1. In practice, it may be substantially greater than 50:1, for instance up to 200:1, e.g up to 150:1. Where we refer to the solvent/precursor ratio it is to be understood that the water component present in the reaction medium forms part of the solvent and is to be included as such in determining the solvent/precursor ratio.

According to a third aspect of the present invention, which may be but is not necessarily used in conjunction with the first and/or second aspect of the invention, there is provided a process for the production of terephthalic acid by the liquid phase oxidation of a precursor of terephthalic acid with oxygen in a reaction medium containing the precursor and a solvent under conditions such that substantially all of the terephthalic acid produced in the oxidation reaction zone is maintained in solution during the reaction, characterised in that the reaction is carried out by producing a flow of the reaction medium through a reaction zone from an inlet region to an outlet region and establishing a temperature profile along the direction of flow through the reaction zone such that the temperature of the reaction medium is greater at the outlet region than at the inlet region.

The production of terephthalic acid by the oxidation of a precursor thereof is a highly exothermic reaction. Conventionally substantially isothermal conditions are maintained in the reactor through removing the heat of reaction by allowing solvent and water of reaction to vaporise and removing the resulting vapour from the reactor. In the process according to this aspect of the present invention, the reaction is carried out under non-isothermal conditions. Thus the heat of reaction need not necessarily be removed or may only be removed to a lesser extent, with the consequence that the temperature within the reaction zone increases from the inlet region to the outlet region of the reaction zone. Typically the subsequent recovery of terephthalic acid from the reaction medium involves cooling of the latter to precipitate the product and separation thereof from the resulting mother liquor which liquor may be recycled to the reaction zone. By allowing the temperature of the reaction medium to increase on passage through the reaction zone, the temperature of recovered mother liquor may be such that little or no further heating of the recovered mother liquor is needed prior to its reintroduction into the reaction zone. Thus, for instance, the temperature of the mother liquor recovered following precipitation and separation of the terephthalic acid may differ from the temperature at the inlet of the reaction zone by no more than about 30° C., more preferably no more than about 20° C.

It is to be understood that we do not exclude the possibility that, in the course of the reaction, some precipitation of terephthalic acid from solution may occur for instance as a result of the temperature at one or more locations along the direction of flow being insufficient to maintain substantially complete dissolution; such precipitation can be compensated for by profiling the temperature along the direction of flow so that precipitated terephthalic acid redissolves at least in part. Also the temperature may be controlled so that any fine particles of terephthalic acid present in any of the liquid phase components supplied to the reaction zone undergo dissolution, at least in part, as the reaction medium progresses through the reaction zone. Such fine particles may be introduced for example as a result of recycle of liquor separated in the course of recovery of terephthalic acid from the reaction medium downstream of the reaction zone.

The temperature profile is typically established by allowing the temperature of the reaction medium to increase, and/or by controlling the temperature rise, due to the exotherm produced by the reaction.

The reaction zone may be formed by a single vessel or conduit or it may comprise a series of sub-zones with each sub-zone formed by a separate vessel or conduit or by separate chambers within a single vessel.

The temperature profile from the inlet region to the outlet region may increase substantially continuously in the direction of flow or it may be of a step-wise character. For instance, where the reaction zone comprises a series of sub-zones there may be provision in at least one such sub-zone for removing or adding heat within that sub-zone in order to establish a temperature profile which, preferably, is consistent with substantially all of the terephthalic acid being maintained in solution throughout the reaction zone.

There may be more than one reaction zone; for instance, two or more reaction zones in parallel each supplied with reactants and solvent and, if desired, the product streams from such multiple reaction zones may be united to form a single product stream.

Where the heat of reaction is removed from the reaction zone (or one or more sub-zone(s) thereof where applicable), it may be removed by heat transfer from the reaction medium to a heat sink across a heat exchange surface, for instance heat exchange with a heat accepting fluid, and/or by introduction of a quenching liquid such as solvent and/or precursor or an immiscible liquid (as referred to in more detail hereinafter) which may be added in one or more stages along the direction of flow of reaction medium through the reactor.

Where a heat accepting fluid is used, it is conveniently passed through one or more flow passages having a wall or walls, the outer surfaces of which are exposed to the reaction medium within the reaction zone. For instance, the heat accepting fluid may be circulated through a coiled tube or tubes immersed in the reaction medium. Alternatively, the reactor may be designed in a manner akin to a tube in shell heat exchanger with the reactants and solvent being passed through the shell and the heat accepting fluid being passed through the tubes internally of the shell.

However, we do not exclude the possibility of effecting the thermal transfer in other ways, for instance by passing the heat accepting fluid through a jacket arrangement at least partly surrounding the reaction zone. For example, the tube in shell design referred to above may be such that the reactants and solvent flow through the tubes while the heat accepting fluid flows through the shell.

The heat accepting fluid may traverse the reaction zone in countercurrent and/or co-current relation with the reaction medium flowing through the reaction zone. Conveniently the passage or passages conducting the heat accepting fluid are arranged to extend internally of the reactor.

Advantageously the heat accepting fluid following heat exchange with the reaction medium is processed to recover thermal, mechanical and/or electrical energy. The power recovered may in part be employed to pressurise air or oxygen to be supplied as oxidant to the process, e.g. by driving a compressor suitable for this purpose. For example, heat transferred to the heat accepting fluid may be converted to mechanical or electrical energy in a power recovery system. One approach is to use the heat accepting fluid to raise steam which can then be superheated and supplied to a steam turbine to recover power.

The heat accepting fluid may be preheated prior to traversing the reaction zone and such preheating may be effected by heat exchange with the product stream resulting from the oxidation reaction.

Conveniently the heat accepting fluid comprises water or oil, e.g. a mineral oil. Alternatively, the heat accepting fluid may comprise the reaction medium or one of the components thereof (i.e. solvent and/or precursor). For instance, the exotherm generated during the reaction may in part be used to preheat incoming reaction medium and in part used to raise the temperature of the reaction medium as it passes through the reaction zone so that substantially all of the terephthalic acid is maintained in solution.

The initial temperature at the commencement of reaction will need to be sufficiently high to ensure that the reaction is initiated but not so high that the temperature rise during the reaction leads to a temperature which results in excessive burning of solvent and aromatics. A typical inlet temperature range would be within the range 80 to 200° C., preferably between 120 and 180° C., e.g. between 140 and 170° C. The temperature of the product stream emerging from the reaction zone will be in excess of the inlet temperature and may be between 180 and 250° C., preferably between 180 and 230° C. (e.g. 190 to 220° C.).

After traversing the reaction zone, substantially all of the terephthalic acid is in solution. The solution may also contain catalyst, and relatively small quantities of intermediates (e.g. p-toluic acid and 4-CBA) and by-products such as colour bodies and trimellitic acid. The desired product, terephthalic acid, may be precipitated, for instance by causing or allowing it to crystallise from the solution in one or more stages, followed by processing of the resulting slurry by solids-liquid separation in one or more stages.

Before the precipitation process, e.g. crystallisation, is implemented and while substantially all of the terephthalic acid and other components are still in solution, the reaction medium may be treated so as to remove certain components. For example, the reaction medium may be treated to remove catalyst metal ions by an ion exchange techniques using for instance a cationic exchange resin or by electrodialysis techniques involving ion exchange membranes.

Because the product/mother liquor slurry resulting from precipitation and separation stages will be relatively thin in view of the relatively high solvent:precursor ratios employed in the process of the present invention, preferably concentration of the product is effected upstream of the solids-liquid separation. Concentration of the slurry may be effected downstream of the crystallisation process using for instance one or more hydrocyclone separators or it may be effected in the course of the crystallisation process by using integrated crystalliser/concentrating apparatus.

The solvent-based mother liquor (which may but need not necessarily contain dissolved catalyst components) recovered following the solids-liquid separation is preferably recycled to the oxidation reaction zone.

The recovery of the terephthalic acid may be effected by conventional crystallisation techniques involving reduction in pressure of the reaction medium. However, such pressure reduction gives rise to a need to repressurise the mother liquor to be recycled to the reaction system.

In another aspect of the present invention, which may be but is not necessarily used in conjunction with the previously mentioned, there is provided a process for the production of terephthalic acid by the liquid phase oxidation of a precursor of terephthalic acid with oxygen in a reaction medium containing the precursor and a solvent under conditions such that substantially all of the terephthalic acid produced in the oxidation reaction zone is maintained in solution during the reaction, characterised in that the terephthalic acid is recovered from the reaction medium by precipitation in such a way as to avoid substantial depressurisation of the reaction medium thereby allowing mother liquor to be recovered at a pressure which is substantially the same as the reactor operating pressure or a pressure close thereto, i.e. about 5 bara or less, preferably about 2 bara or less, lower than the operating pressure of the reactor system.

In each of the above-mentioned and following aspects of the invention disclosed herein, prior to re-introduction into the oxidation reaction zone, the mother liquor may be heated by heat exchange with the reaction medium after the latter has emerged from the reaction zone and/or while the latter is traversing the reaction zone, thereby cooling the reaction medium.

Usually the resulting precipitate will contain no more than 5000 ppm by weight of 4-CBA. Preferably the terephthalic acid precipitated from the reaction medium contains no more than 3000 ppm, more preferably no more than about 1000 ppm and most preferably no more than about 500 ppm (e.g. 20 to 300 ppm), by weight of 4-CBA.

Cooling of the reaction medium, with consequent precipitation of the terephthalic acid, is advantageously carried out, preferably under superatmospheric conditions, in such a way that the temperature of the resulting slurry undergoing solids-liquid separation is within the range of 120 to 180° C., more preferably about 130 to about 175° C. and most preferably about 140 to about 170° C. Although carrying out the solids-liquid separation at such a high temperature results in a substantial proportion of the terephthalic acid remaining in solution, it has been found that the levels of the major impurities in the recovered product reduce as temperature initially falls from the temperature at which the reaction medium is withdrawn from the reaction zone and then increase as the temperature falls further.

According to a further aspect of the invention, which may be but is not necessarily used in conjunction with other aspects of the invention disclosed herein, there is provided a process for the production of terephthalic acid by the liquid phase oxidation of a precursor of terephthalic acid with oxygen in a reaction medium containing the precursor and a solvent under conditions such that substantially all of the terephthalic acid produced in the oxidation reaction zone is maintained in solution during the reaction, the reaction medium thereafter being cooled to precipitate terephthalic acid which is recovered by solids-liquid separation, characterised in that the solids-liquid separation is carried out at a temperature within the range of about 120 to about 180° C., more preferably about 130 to about 175° C. and most preferably about 140 to about 170° C.

According to yet another aspect of the present invention, which may be but is not necessarily used in conjunction with other aspects of the invention disclosed herein, there is provided a process for the production of terephthalic acid by the liquid phase oxidation of a precursor thereof in a solvent, the liquid phase oxidation being carried out in a reaction zone in such a way that substantially all of the terephthalic acid produced is maintained in solution in the reaction medium during the reaction, characterised in that the oxidant is introduced into the reaction zone at two or more locations spaced apart in the direction of flow of the reaction medium from an inlet region of the reaction zone to an outlet region thereof.

This aspect of the invention is particularly applicable to the case where the reaction zone is formed, at least in part, by a plug flow reactor and is particularly beneficial where the oxidant is in the form of substantially pure oxygen or an oxygen enriched gas.

Such locations are conveniently so positioned relative to the bulk flow of solvent and reactants through the oxidation zone that oxidant is introduced to the reaction at an initial location and at least one further location downstream of said initial location. The oxidant may be introduced substantially continuously over a length of the reaction medium flow path through the reaction zone and/or sub-zone(s); for example, the oxidant may be introduced by means of a perforated pipe immersed in the reaction medium and extending in the direction of flow, the number, spacing and distribution of the perforations being such that the oxidant is introduced at substantially all points along said length of the reaction zone and/or sub-zone(s).

The oxidant in each of the foregoing aspects of the invention is conveniently molecular oxygen, e.g. substantially pure oxygen, air or other oxygen containing gas (i.e. gas containing oxygen as the major or minor constituent thereof), or oxygen dissolved in liquid. The use of substantially pure oxygen as the oxidant has the benefits of avoiding gas voidage and disruption of plug flow profile while affording high oxygen mass transfer rates required for intensified reaction at modest operating pressures.

The oxygen may be combined with a diluent gas, such as carbon dioxide, which is more soluble in the solvent than nitrogen. The diluent gas may be derived for instance from the vent gas produced during the oxidation reaction. Where the diluent gas is derived from the vent gas, the vent gas will preferably have been treated, e.g. by high temperature catalytic combustion, to convert any methyl bromide present to HBr and $Br_2$ and may be recycled, at least in part, without removing its HBr content since HBr can be employed as a catalyst component in the oxidation reaction. For example, following treatment to convert MeBr to HBr and $Br_2$, part of the vent gas may be diverted for dilution of the oxygen supply to the reaction while the remainder may be processed further, e.g. for disposal or use as a fluidising medium for conveying purposes. The diverted portion of the treated off gas may be cooled (for instance, by heat exchange with the vent gas upstream of the MeBr conversion step) and recompressed (before or after admixture with the oxygen supply) sufficiently to allow it to be reintroduced in the oxidation reaction. The processing of the remaining vent gas may comprise supply to a power recovery system such as an expander and scrubbing (upstream and/or downstream of the expander) to remove any residual pollutants such as HBr and $Br_2$.

Instead of molecular oxygen, the oxidant may comprise atomic oxygen such as a compound, e.g. a liquid phase compound at room temperature, containing one or more oxygen atoms per molecule. One such compound for example is hydrogen peroxide.

Besides the solvent:precursor ratio, various other parameters such as temperature and water content also need to be taken into account in order to ensure that substantially all of the terephthalic acid produced is maintained in solution during the reaction.

The elevated pressure conditions under which the reaction is carried out will normally be selected such that the reaction medium is maintained in the liquid phase during the reaction (non-boiling conditions). Usually the reaction will be carried out at a pressure in the range of 10 bara to 100 bara, typically 20 bara to 80 bara, depending on the nature of the oxidant; for instance if the reaction is carried out using dissolved oxygen, the pressure is typically about 60 to about 80 bara where substantially pure oxygen is employed but may be greater, e.g. above 100 bara where the oxygen and a diluent are dissolved in the reaction medium.

According to a further aspect of the invention, which may be but is not necessarily used in conjunction with other aspects of the invention disclosed herein, there is provided a process for the production of terephthalic acid by the liquid phase oxidation of a precursor of terephthalic acid with oxygen in a reaction medium containing the precursor and a solvent under conditions such that substantially all of the terephthalic acid produced in the oxidation reaction zone is maintained in solution during the reaction, characterised in that the total oxidation reaction volume A, in $m^3$, associated with the reaction zone, the 4-CBA content B of the recovered terephthalic acid in ppm w/w, and the amount of terephthalic acid C recovered from the oxidation reaction, in te/hr, are related by the formula:

$$(A*B)/C<4,000.$$

The term "total oxidation reaction volume" is to be understood to comprise the total volume of the reactor vessel or vessels (in parallel and/or series) forming the reaction zone, including any vapour head space provided in such vessel or vessels, e.g. for liquid/vapour disengagement.

Preferably the the relationship is such that:

$$(A*B)/C<3,000.$$

Usually, in the context of this aspect of the invention, the 4-CBA content of the recovered terephthalic acid will be no greater than about 5,000 ppm w/w and preferably is no greater than about 3,000 ppm w/w, more preferably no greater than about 1,000 ppm w/w, and may be lower than about 500 ppm w/w, e.g. in the range of about 20 to about 300 ppm w/w. Also the rate of production of terephthalic acid will typically be in excess of 20 te/hr.

This aspect of the invention may be implemented by operating the terephthalic acid process in accordance with the various aspects of the invention; for instance, by carrying out the production process in an oxygen-fed continuous plug flow (or quasi-plug flow) regime in non-boiling conditions. For instance, a substantially pure oxygen-fed single plug flow reactor in accordance with the present invention operated to produce terephthalic acid product at a rate of 60 te/hr with a 4-CBA content of 250 ppm w/w can be implemented by a design having a total oxidation reaction volume of less than 160 $m^3$ and, in this event, (A*B)/C<1,000. In contrast, a conventionally designed oxidation reactor currently in operation and designed to produce 60 te/hr crude terephthalic acid with a 4-CBA content of about 2500 ppm w/w requires a total oxidation reaction volume in excess of 400 m³ and therefore, in this case, (A*B)/C>16,000, which clearly demonstrates the significant reduction in reactor volume that may be achieved by virtue of the present invention. In the case of a conventional single stage oxidation process using multiple reactors operating with high catalyst concentration and high temperature (and consequent high levels of acetic acid burning) to produce fibre grade terephthalic acid with a 4-CBA content of 500 ppm and at a rate of 60 te/hr, the total oxidation reaction volume required is of the order of about 800 m³ which gives a value greater than 6,600 for the relationship (A*B)/C.

In a related aspect of the invention, plant for the production of terephthalic acid by the liquid phase oxidation of a precursor thereof and operationally designed to produce terephthalic acid having a 4-CBA content B of less than about 5,000 ppm w/w at a production rate C of at least 20 te/hr, characterised in that the total oxidation reaction volume A, in m³, of the vessel or vessels in which the oxidation reaction is carried out satisfies the following condition:

$$A < (4,000 \cdot C)/B.$$

The process in any one of the foregoing aspects of the invention will normally be carried out in the presence of an oxidation catalyst. Where employed, the catalyst may be soluble in the reaction medium comprising solvent and the terephthalic acid precursor(s) or, alternatively, a heterogeneous catalyst may be used. The catalyst, whether homogeneous or heterogeneous, typically comprises one or more heavy metal compounds, eg. cobalt and/or manganese compounds, and may optionally include an oxidation promoter such as bromine or acetaldehyde. For instance, the catalyst may take any of the forms that have been used in the liquid phase oxidation of terephthalic acid precursors such as terephthalic acid precursor(s) in aliphatic carboxylic acid solvent, eg. bromides, bromoalkanoates or alkanoates (usually C1–C4 alkanoates such as acetates) of cobalt and/or manganese. Compounds of other heavy metals such as vanadium, chromium, iron, molybdenum, a lanthanide such as cerium, zirconium, hafnium, and/or nickel may be used instead of cobalt and/or manganese. Advantageously, the catalyst system will include manganese bromide ($MnBr_2$). The oxidation catalyst may alternatively or additionally include one or more noble metals or compounds thereof, e.g. platinum and/or palladium or compounds thereof, for example in highly divided form or in the form of a metal sponge. The oxidation promoter where employed may be in the form of elemental bromine, ionic bromide (eg. HBr, NaBr, KBr, $NH_4Br$) and/or organic bromide (eg. bromobenzenes, benzyl-bromide, mono- and di-bromoacetic acid, bromoacetyl bromide, tetrabromoethane, ethylene-di-bromide, etc.). Alternatively the oxidation promoter may comprise a ketone, such as methylethyl ketone, or aldehyde, such as acetaldehyde.

Where the catalyst is in heterogeneous form, it may be suitably located within the reaction zone so as to secure contact between the continuously flowing reaction medium and the catalyst. In this event, the catalyst may be suitably supported and/or constrained within the reaction zone to secure such contact without unduly constricting the flow cross-section. For instance, the heterogeneous catalyst may be coated on or otherwise applied to, or embodied in, static elements (eg. elements forming an openwork structure) positioned within the reaction zone so that the reaction medium flows over the same. Such static elements may additionally serve to enhance mixing of the reactants as they pass through the reaction zone. Alternatively the catalyst may be in the form of mobile pellets, particles, finely divided form, metal sponge form or the like with means being provided if necessary to confine the same to the reaction zone so that, in operation, the catalyst pellets etc become suspended or immersed in the reaction medium flowing through the reaction zone. The use of a heterogeneous catalyst in any of these ways confers the advantage of being able to confine the catalysis effect to a well-defined zone so that, once the reaction medium has traversed the zone, further oxidation takes place at a reduced rate or may be significantly suppressed. Also, provision for catalyst recovery may be avoided.

The support for the oxidation catalyst can be less catalytically active or even inert to the oxidation reaction. The support may be porous. In general, the catalyst support materials will be substantially corrosion resistant and substantially oxidation resistant under the conditions prevailing. Thus, depending on the prevailing conditions, the catalyst support material can be selected from for example titania, silica, alumina, silica alumina, alpha alumina, gamma alumina, delta alumina, and eta alumina, mullite, spinel, andzirconia. Supports comprising alpha alumina, gamma alumina, silica, or silica alumina are preferred.

The support component of the oxidation catalyst may be pure or a composite of materials, the latter being employed for example to impart desired chemical or physical characteristics to the catalyst. For instance, the oxidation catalyst may comprise a substrate with high attrition resistance and a substrate coating having high surface area. Conventional impregnation techniques may be used to fabricate the same. Materials for use as the substrate will generally be substantially corrosion resistant and substantially oxidation resistant under the conditions prevailing. Thus, depending on the prevailing conditions, the substrate material can be selected from alpha alumina, mullite and spinel. Materials for use as a composite substrate coating are silica, alumina, titania, zirconia, alpha alumina, gamma alumina, delta alumina and eta alumina.

The invention will now be described by way of example only with reference to the accompanying drawings illustrating application of the processes according to various aspects of the invention to the production of terephthalic acid. In the drawings.

Figure 1:
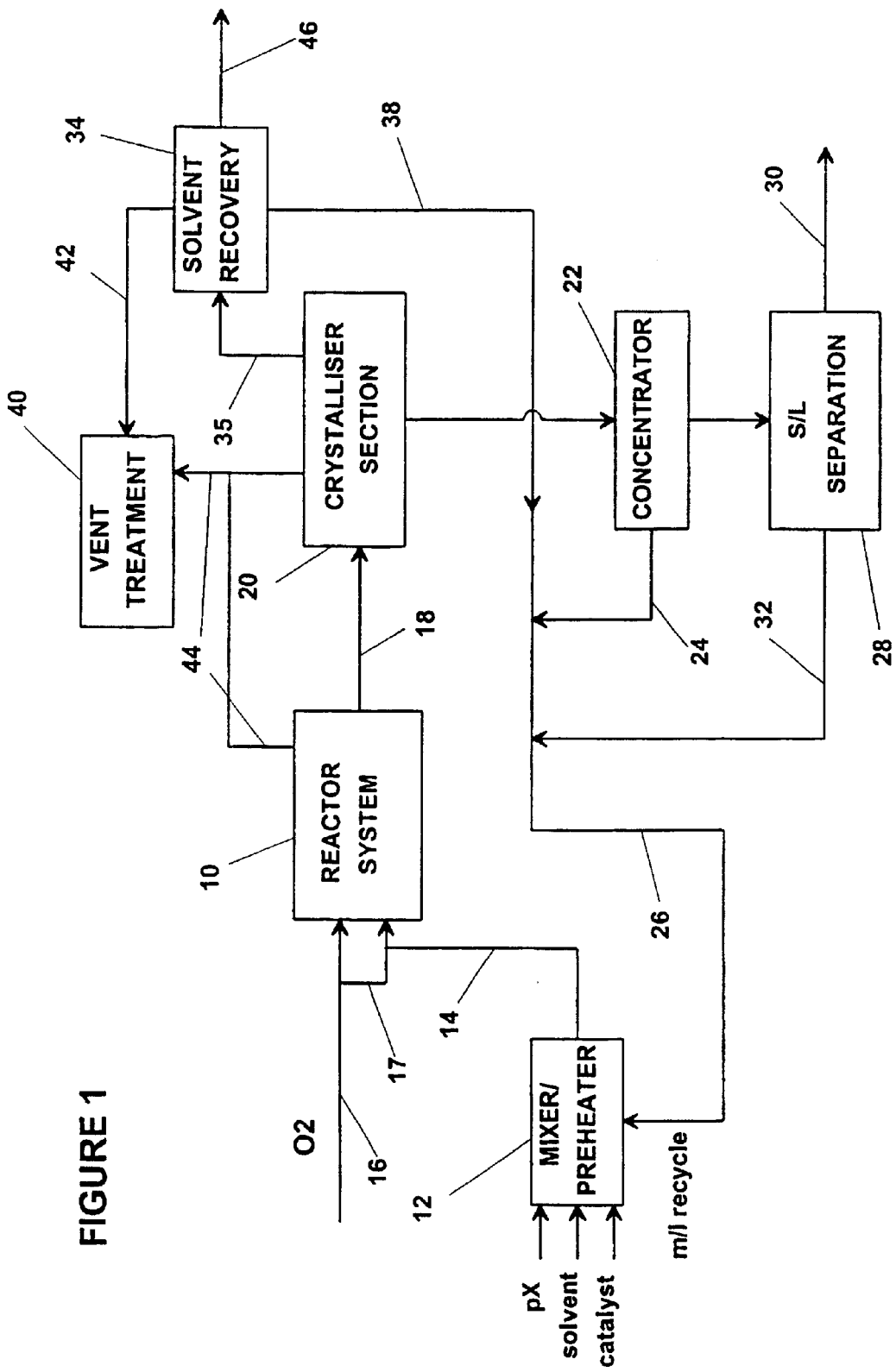
FIG. 1 is a block diagram showing the overall oxidation process.

Referring to FIG. 1, terephthalic acid is produced in a reactor system 10 by the liquid phase oxidation of a precursor thereof, e.g. paraxylene, in a solvent such as acetic acid, the oxidation being carried out in the presence of a catalyst system. The reactor system 10 may take various forms such as a single plug flow reactor, two or more plug flow reactors arranged in series, a plug flow reactor in combination with one or more continuous stirred tank reactors, or two or more continuous stirred tank reactors in series and arranged so as to approximate plug flow. Some examples of the possible reactor system configurations will be described below. Precursor, make-up solvent, make-up catalyst (e.g. comprising cobalt and manganese compounds together with bromine as an oxidation promoter) and recovered mother liquor and solvent components are mixed in mixer and preheater section 12 to produce a reaction medium in which the solvent (fresh and recovered) to precursor ratio in the mixture is substantially higher than that used in the conventional oxidation of paraxylene terephthalic acid by liquid phase oxidation. At least part of the preheat (where needed) may be provided by the recovered mother liquor and solvent under steady state operating conditions of the system. The heat supplied through the recovered mother liquor may be sufficient to eliminate the need for an external heat source under steady state conditions although, in this event, an external source will still be needed on start-up. Typically the solvent:precursor ratio is of the order of about 70:1 (on a weight basis). The mixture is supplied via line 14 to the inlet region of the reaction system. The temperature of the mixture supplied to the reaction system is typically at a temperature of about 150° C. and is pumped to a suitable pressure to ensure that boiling of reaction medium during the reaction is substantially prevented. Instead of mixing the liquid phase components in mixer 12, they may instead be preheated but kept separate until introduction into the reactor system (in which case unit 12 may simply be a preheater) and supplied to the reactor system 10 as two or more separate feeds 14 to be mixed at the inlet region of the reactor system 10 (see FIG. 1A for an example of such a scheme).

Oxygen is supplied via line 16. The oxygen supply may take various forms including substantially pure oxygen, air, oxygen enriched air, gas containing oxygen and a diluent such as nitrogen or carbon dioxide etc. Although the oxygen supply is depicted by a single line 16 entering the reaction system, the method of supplying oxygen and the nature of the oxygen supply in terms of its concentration may vary as will become apparent from the more specific embodiments described below. Also while the source of oxygen is shown as being supplied to the reactor system separately from the solvent/paraxylene reaction medium, it is preferably predissolved at least in part (see line 17) in the reaction medium or one or more components thereof (e.g. acetic acid and/or mother liquor recycle) upstream of the reactor system or the mixer/preheater section 12, irrespective of the oxygen source used but particularly where substantially pure oxygen, or oxygen diluted with an inert gas, is used.

The solvent/precursor/catalyst reaction medium passes through the reactor system, preferably as a plug flow or plug flow approximation, from the inlet region to an outlet region at which a product stream is withdrawn via line 18. The reaction is carried out in such a way that substantially all of the terephthalic acid formed during passage of the solvent/precursor mixture through the reaction is maintained in solution, thereby maintaining intermediates such as paratoluic acid and 4-CBA in solution during the reaction and hence available for reaction. In this manner, it is possible to secure a product having a relatively low 4-CBA content.

The product stream is passed via line 18 to a crystallisation section 20 in which precipitation of the product, terephthalic acid, is effected to form a thin slurry of terephthalic acid in a mother liquor which mainly comprises the solvent employed and some water, dissolved catalyst components, terephthalic acid, intermediates thereof and by-products formed in the reaction. The crystallisation process involves reducing pressure and temperature and at the end of the process the slurry pressure may range from below atmospheric pressure to pressures substantially above atmospheric pressure, preferably the latter.

The temperature at which the crystallisation process is terminated may be selected so that the mother liquor recovered subsequently from the slurry is at a suitable temperature such that, when mixed with make-up solvent and precursor, the mixed stream has a predetermined temperature corresponding to the desired inlet region temperature of the reaction zone. Water is produced in the oxidation reaction; one method of removing at least part of the water of reaction is to use a pressure rectifier/distillation column in conjunction with the crystallisation section; for example by supplying the flash vapour from at least one of the crystalliser vessels, at elevated pressure, directly to a distillation column for separating solvent (as bottoms product) from the water (overheads product in the form of steam). The pressurised steam overheads may then be used in a power recovery system by means of a steam condensing turbine. One example of such a scheme will be described in more detail below with reference to FIG. 6.

Where the terephthalic acid is precipitated by a crystallisation process involving reduction in the pressure of the reactor product stream below its saturated vapour pressure to initiate solvent removal by flashing and solvent cooling, following recovery of the terephthalic acid, at least the bulk of the residual mother liquor is re-pressurised and recycled to the reactor. In an alternative approach aimed at avoiding having to repressurise the mother liquor recycle stream, the terephthalic acid may be precipitated by cooling the reactor product stream without reducing its pressure. Heat is then removed via a heat exchange surface and used in, for example, steam raising or process heating etc. In such an arrangement, on cooling the terephthalic acid will tend to foul the heat exchanger surface, reducing its effectiveness. This fouling can be managed by employing a surface scraped heat exchanger device.

Another alternative with the aim of reducing the extent to which re-pressurisation of the mother liquor recycle stream is necessary involves precipitating the terephthalic acid from the reaction medium by solvent removal, without cooling the solvent. Solvent removal can be effected by forcing it through a semi-permeable membrane (permeable to acetic acid and water and optionally to catalyst and reaction impurities, but impermeable to terephthalic acid). On solvent removal, terephthalic acid precipitation is initiated and fouling of the membrane pores, which would otherwise reduce membrane effectiveness, can be countered by, for example, design for high shear across the membrane surface and/or staging of membranes in series with intermediate vessels in which the bulk of the crystallisation occurs. Because pressure drop through the membrane system is not substantial, the pumping cost for effecting recycle of mother liquor can be reduced.

Following the crystallisation process, the slurry strength will be significantly lower than is the case in the conventional production of terephthalic acid—i.e. because of the high solvent:precursor ratio employed. Desirably therefore, before carrying out solids-liquid separation, the slurry is concentrated. This can be effected downstream of the crystallisation section in a concentration section 22 which may, for example, comprise one or more hydrocyclone stages producing a thickened underflow stream comprising the major part of the terephthalic acid crystal mass in the slurry and mother liquor and an overflow stream comprising mother liquor in which terephthalic acid fines may be suspended. Concentration of the slurry by means of one or more hydrocyclones is particularly expedient in view of the relatively low cost of such devices; however, other devices may be used instead such as one or more centrifuges (nozzle, decanter etc), a filter or filters (including cross-flow microfiltration), or gravity clarification/thickening devices either separate from or incorporated in the crystalliser (as described hereinafter).

The overflow stream from the concentration section 22 is routed via lines 24 and 26 for recycle to the mixer/preheater 12. The concentrate is supplied to a solids-liquid separation section 28 in which the terephthalic acid crystals are separated from the mother liquor, the solids-liquid separation being carried out using for example one or more filtration devices operating under superatmospheric, atmospheric or sub-atmospheric conditions, with or without washing facilities, such as described in our prior published International Patent Applications Nos. WO 93/24440 and WO 94/17982 (the entire disclosures of which are incorporated herein by this reference). Thus, for example the integrated solids separation and water washing apparatus may comprise a centrifuge, a belt filter unit, a rotary cylindrical filter unit operated with the slurry side under pressure, or a drum filter unit (e.g. a BHS-Fest pressure filter drum formed with a plurality of slurry receiving cells in which the mother liquor is displaced from filter cake by water under hydraulic pressure supplied to the cells). After filtering the slurry, the recovered terephthalic acid may be dried. If not already at atmospheric pressure, the filter cake of terephthalic acid may be transferred to a low pressure zone (e.g. atmospheric pressure) for drying via a suitable pressure letdown device such as a lock hopper arrangement, a rotary valve, a ram-type pump, a screw feed device or a progressive feed device such as a progressive cavity pump of the type used to pump cold pastes of high solids contents.

The temperature of separation and the degree of washing required will be dependent on the levels of impurities generated in the reaction and the required product specification. Although, in general, it will be desirable to produce terephthalic acid which is sufficiently pure to render further purification unnecessary (e.g. by oxidation and/or hydrogenation of an aqueous solution of the terephthalic acid to convert 4-CBA to terephthalic acid or to paratoluic acid, as the case may be), we do not exclude the possibility of carrying out such purification in the process of the present invention. Following solids-liquid separation, the product may be recovered via line 30 for drying and use in the downstream production of polyester by esterification with a diol (e.g. ethylene glycol) without necessarily requiring intervening chemical purification. Drying of the product may be carried out in for example a rotary steam tube drier or a fluidised bed drier.

The mother liquor obtained as filtrate from the solids-liquid separation section 28 is routed via lines 32 and 26 for recycle to the mixer/preheater 12. The mother liquor may contain some solid phase terephthalic acid in the form of fines. This fines content may at least in part redissolve in the reaction medium as a result of preheating or within the reaction system; however, even if some of the fines content remains undissolved as it passes through the reaction system, this will normally be tolerable since the fines will tend to be relatively pure in contrast with the fines produced in the conventional process for the production of terephthalic acid. Although not illustrated in FIG. 1, the recovered mother liquor (lines 32 and 26) may be heated before return to the mixer 12 using a heat exchanger-to effect heat transfer from the product stream on line 18 to the mother liquor recycle. Alternatively, it may be desirable to cool the mother liquor (e.g. where the mother liquor is used as a vehicle for pre-dissolving oxygen) in which case the mother liquor may for example be brought into heat exchange relation with the feed or one of the feeds 14 to the reactor system so as to effect heating of the feedstream or feedstreams.

Part of the solids recovered downstream of the crystallisation process may be recycled back to one or more of the crystallisers in order to "seed" the solution and nucleate and/or promote particle growth. For instance, part of the fines-containing overflow stream or the thickened underflow stream from the concentration section may be recycled to the crystallisation process for this purpose.

The crystallisation process typically involves flashing off solvent and water from the slurry, the water being produced as a reaction by-product. The resulting vapour and/or condensate is supplied via line 35 to a solvent recovery section 34. Solvent recovered in the solvent recovery section is routed via lines 38 and 26 to the mixer/preheater 12 while gases and other volatiles are passed to a vent treatment system 40 via line 42 along with any volatiles and gases, including unreacted oxygen, recovered from the reaction system and/or crystalliser section via line 44. Where the reactor system is operated under sufficiently high pressure conditions to secure a single phase regime throughout the reaction, no vent gases are obtained from the reactor system; instead the gaseous components are removed by venting when they come out of solution in the crystallisation section. Water separated from the solvent in solvent recovery section 34 is routed via line 46 to an effluent treatment plant.

Figure 1A:
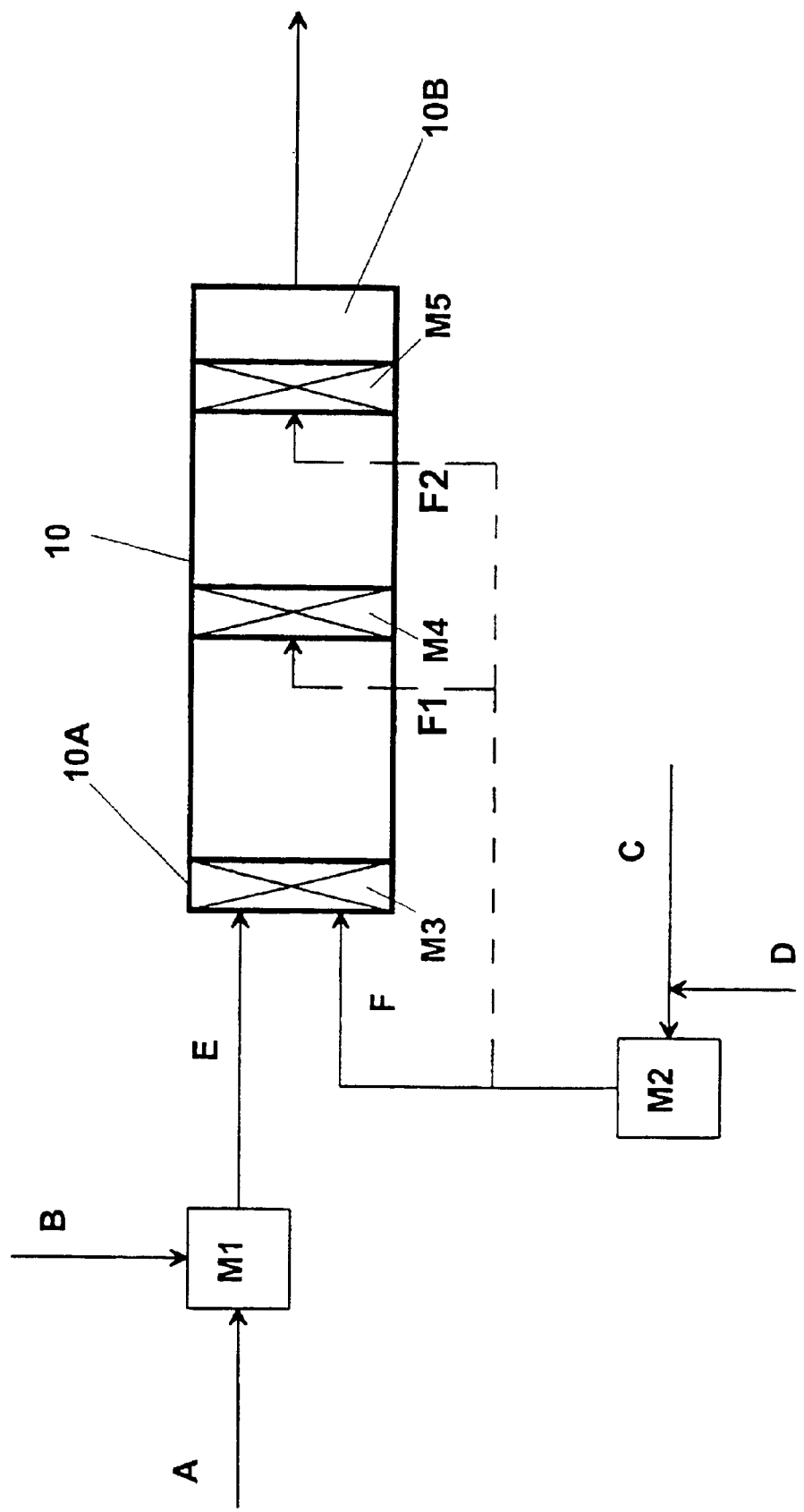
FIG. 1A is a view showing one method of combining the various feeds to form the reaction medium.

The method of introducing the oxygen into the reaction may vary. In a preferred embodiment of the invention the oxygen or oxygen-containing gas is introduced into the reaction medium in such a way that substantially all of the oxygen or oxygen-containing gas is dissolved in the reaction medium so that the reaction can be conducted under single phase conditions with those components which, in a conventional terephthalic acid production process, would otherwise be in the gas phase and solid phase being present in dissolved form in the liquid phase reaction medium. FIG. 1A illustrates one scheme for achieving this. In this case, the reactor 10A is supplied with the following liquid phase components:

A. paraxylene and acetic acid solvent (liquid phase);
    B. make-up catalyst in acetic acid solvent (liquid phase);
    C. mother liquor recovered from the process (liquid phase); and
    D. oxygen or oxygen-containing gas (gas phase).

Feeds A And B, which are relatively small in volume compared with feed C, are pumped to system pressure and then initially mixed together in mixer M1 and preheated if necessary during, before or after mixing, thereby producing combined feed E. Feed E is fed into the inlet region 10A of the reactor system. Oxygen in excess of the stoichiometric amount required for the reaction is added, via feed D, to the mother liquor feed C which is under system pressure and, if necessary, after addition of the oxygen is preheated, and the resulting oxygen-containing liquid, feed F, is introduced into the inlet region 10A. The oxygen may for instance be added as a single jet into the mother liquor recycle stream immediately upstream of a static mixer M2. The static mixer M2 is designed to ensure that: by continuous mixing of the mother liquor stream, there are no localised high concentrations of oxygen in solution; maximum bubble size is controlled by preventing bubble coalescence; and bubbles are distributed uniformly throughout the mother liquor recycle stream so as to minimise the time taken to dissolve all of the gas in the liquid stream. The inlet region 10A includes a mixing arrangement M3, e.g a static mixer, for ensuring thorough mixing of the feeds E and F thereby forming the reaction medium.

The system operating pressure, i.e. the pressure to which the feeds E and F are pressurised, is selected so that all of the oxygen or oxygen-containing gas introduced enters into solution into the liquid phase reaction medium while ensuring that boiling of the reaction medium is prevented. Where pure oxygen is employed as the oxygen source, the system operating pressure may typically be in excess of about 60 bara and will be correspondingly increased where a diluent is present. For instance, where the oxygen is supplied in the form of a gas containing 80% oxygen and 20% nitrogen, the system operating pressure will be typically in excess of about 75 bara. The temperature of the feeds E and F will be such that, when combined, a desired reaction medium temperature (e.g. 150° C.) is secured at the inlet of the reactor system 10 consistent with initiating the oxidation reaction.

The acetic acid/paraxylene ratio will be determined by solvent introduced via feeds A and B and also by acetic acid recycled via the mother liquor feed C. This ratio will be such that substantially all of the terephthalic acid produced in the ensuing reaction is maintained in solution throughout the reaction zone, taking into account the fact that more and more terephthalic acid is produced as the reaction medium progresses towards the outlet region 10B of the reactor system and also that the temperature of the reaction medium increases since the reactor system is operated non-isothermally resulting in a temperature increase from the inlet region 10A to the outlet region 10B. The temperature profile produced may be tailored and one such means for controlling the temperature profile is to introduce feed F into the reactor system 10 in stages rather than in one-shot at the inlet region 10A. Thus, as illustrated in phantom outline in FIG. 1A, the feed F may be split into separate feeds F, F1, F2 . . . with feed F being introduced at the inlet region 10A and the remaining feeds F1, F2 . . . being injected as quench feeds into the reaction medium at different points along the path of flow of the reaction medium through the reactor system. At each injection point, suitable mixing arrangements M4, M5 will be provided to ensure thorough mixing of the injected liquid with the remaining reaction medium. Where the reactor system comprises two or more separate reactor vessels, the feeds F1, F2 . . . may be conveniently injected into the reaction medium at the transitions between successive reactor vessels.

In practice, the mother liquor feed C is the most suitable vehicle for the introduction of the oxygen into the reaction as it will normally constitute the bulk of the reaction medium during steady state operating conditions; however, we do not exclude the possibility of oxygen being introduced by way of one or more of the other feeds to the reactor system either instead of the mother liquor feed or in addition thereto.

Figures 2, 3:
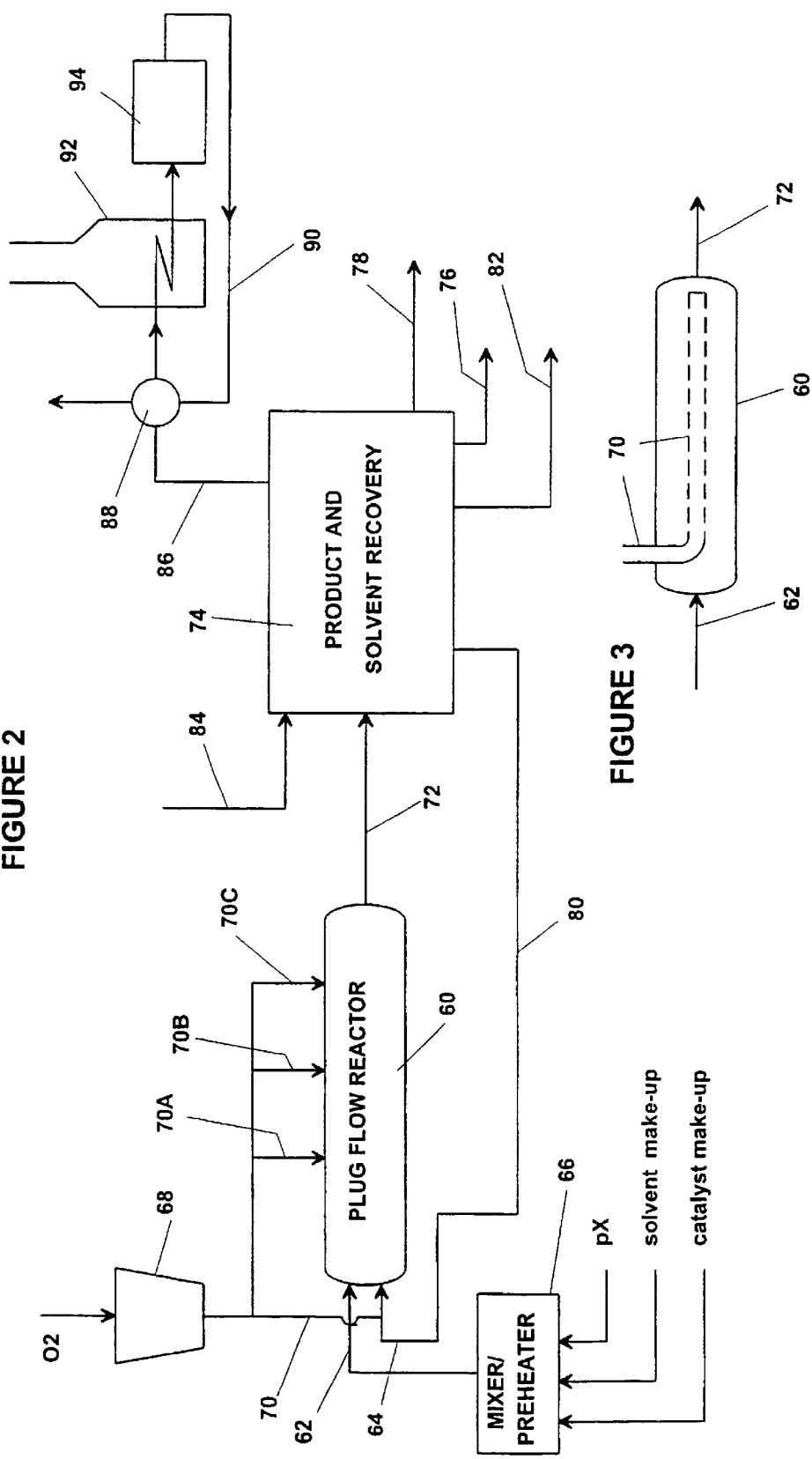
FIG. 2 is a flow sheet illustrating one form of oxidation reactor scheme that may be used in the process of the present invention employing substantially pure oxygen or oxygen enriched gas as the oxidant.
FIG. 3 illustrates a modification of the oxidation reactor shown in FIG. 2.

Referring now to FIG. 2, this illustrates one form of the process described generally with reference to FIG. 1 in which the reactor system is in the form of an adiabatic plug flow reactor 60 having an inlet region to which the reactants are supplied for mixing, the liquid phase reaction medium being produced by combining a mixture of paraxylene, fresh solvent and make-up catalyst supplied via line 62 from mixer/preheater 66, and recycled mother liquor feed on line 64. The oxidant (in this case substantially pure oxygen) is supplied via compressor 68 and line 70 and is combined with the mother liquor recycle feed 64. The reactants are combined with suitable intensive mixing so as to produce a single phase with the oxygen dissolved in the liquid phase. Typically the liquid phase reaction medium is pumped to a pressure of the order of 60 bara and the oxygen is compressed to a pressure in excess of 60 bara to facilitate its introduction into the liquid phase. As in the case of the embodiment of FIG. 1, the reaction medium comprises a mixture of paraxylene (pX), solvent-based mother liquor and solvent recovered downstream of the reactor system, solvent make-up and catalyst make-up. Typically the reaction medium/oxidant mixture supplied to the inlet 62 of the reactor system is at a temperature of the order of 150° C. Single phase operation of the reactor system can lead to advantages in terms of reduction/suppression of methyl acetate formation where acetic acid is employed as solvent, and lower levels of solvent burn can be achieved compared with conventional reactors. Moreover the use of oxygen rather than air results in a substantial reduction in the volume of gas vented during the subsequent crystallisation process.

The entire oxygen supply for the reaction may be introduced at the inlet region of the reaction system 60 in which case, to achieve single phase conditions in which the oxygen is dissolved in the liquid phase, this would require operation of the reactor at high pressure (e.g. of the order of 60 to 100 bara). If desired, the reactor pressure can be reduced significantly by distributing the oxygen supply along the direction of flow through the reactor 60. Thus, as shown in FIG. 2, part of the oxygen is supplied by line 70 and the remainder is injected (with suitable intensive mixing to secure single phase conditions) at a series of locations along the length of the reactor 60 via N injection points 70A, 70B and 70C (where N is equal to one or more). In a variation as illustrated in FIG. 3, the distribution of the oxidant may be made substantially continuous by introducing it via a perforated conduit or the like extending internally and lengthwise of the reactor 60. By introducing the oxidant progressively as illustrated in FIG. 2 or FIG. 3, the amount of oxidant supplied to the reaction at a particular location can be tailored to the oxygen requirement at that location and to ensure that there are no oxygen starved zones within the reactor. Moreover, the reactor pressure can be reduced provided that it is kept at a level sufficient to prevent boiling of the reaction medium during the reaction.

Where the solvent:paraxylene ratio of the mixture supplied to the inlet of the reactor 60 is for example of the order of about 60:1, the adiabatic temperature rise in the course of the reaction is about 70° C. The reaction exotherm may be removed by allowing the temperature to rise from an inlet temperature of for example 150° C. at the reactor inlet 62 to about 220° C. at the reactor outlet 72 without the need to remove heat, e.g. by indirect heat transfer or quenching by introduction of cooler liquid (i.e. reaction medium or heat carrier). However, it will be understood that the invention, including the embodiment of FIG. 2, is not limited to removal of the exotherm solely by allowing the temperature to rise from the inlet to the outlet of the reactor, and that any suitable heat removal method may be employed to remove the heat of reaction at least in part.

The product stream withdrawn from the exit 72 of the plug flow reactor is processed in a product and solvent recovery section 74 corresponding generally to the plant sections 20, 22, 28 and 34 described with reference to FIG.

1 with recovered product, recovered water and recovered mother liquor, mother liquor purge being depicted by references 76, 78, 80 and 82 respectively. Because in this embodiment, substantially pure oxygen is employed as the oxidant, nitrogen or other inert gas is supplied to the crystallisation process via line 84 to ensure that the vent gas recovered via line 86 is not flammable. The nitrogen will usually be supplied to the headspace of at least the first (highest temperature, pressure) crystallisation vessel in the crystallisation train. The vent gas stream 86 is passed through heat exchanger 88 where it is preheated by hot treated vent gas supplied via line 90 before being heated in furnace 92 and then subjected to catalytic combustion in unit 94 in order to destroy pollutants such as carbon monoxide and organics which are convertible to $CO_2$ and water. The treated gas, following passage via line 90 through heat exchanger 88 can be discharged, if necessary after scrubbing with water or alkali to remove any remaining pollutants such as bromine and HBr arising from catalytic combustion of any methyl bromide present in the vent gas stream 86.

In a variation of the embodiment of FIG. 2, there may be two or more plug flow reactors connected in series, optionally with multiple injection of oxidant into one or more of the series connected reactors. For example, product-containing stream from the first reactor may be passed directly to the next reactor (and so on where more than two plug flow reactors are provided). A quenching medium may be introduced into one or more of the reactors downstream of the first in order to control the temperature profile of the reactor system as a whole, consistent with maintaining substantially all of the terephthalic acid formed in solution. The quenching medium will usually comprise the solvent employed in the reaction (e.g. mother liquor as described with reference to FIG. 1A), optionally with oxygen predissolved therein. In another variation, the heat controlling medium introduced into one or more of the reactors downstream of the first reactor may, depending on the temperature profile to be established through the reactor system, serve to heat rather than cool the product-containing stream undergoing transfer from the preceding reactor.

In the foregoing description, the catalyst employed is dissolved in the solvent medium supplied to the oxidation reaction; however, as discussed previously, a heterogeneous catalyst may be employed. Preferably the catalyst system includes zirconium. For instance, supplementing the cobalt by 15% by weight of zirconium has been found to produce a marked reduction in 4-CBA content compared with identical conditions (residence time, feed composition and temperature) but without such supplement—i.e. about 100 ppm 4-CBA with zirconium substitution in the catalyst system compared with 250 ppm 4-CBA without zirconium supplement.

Figure 4:
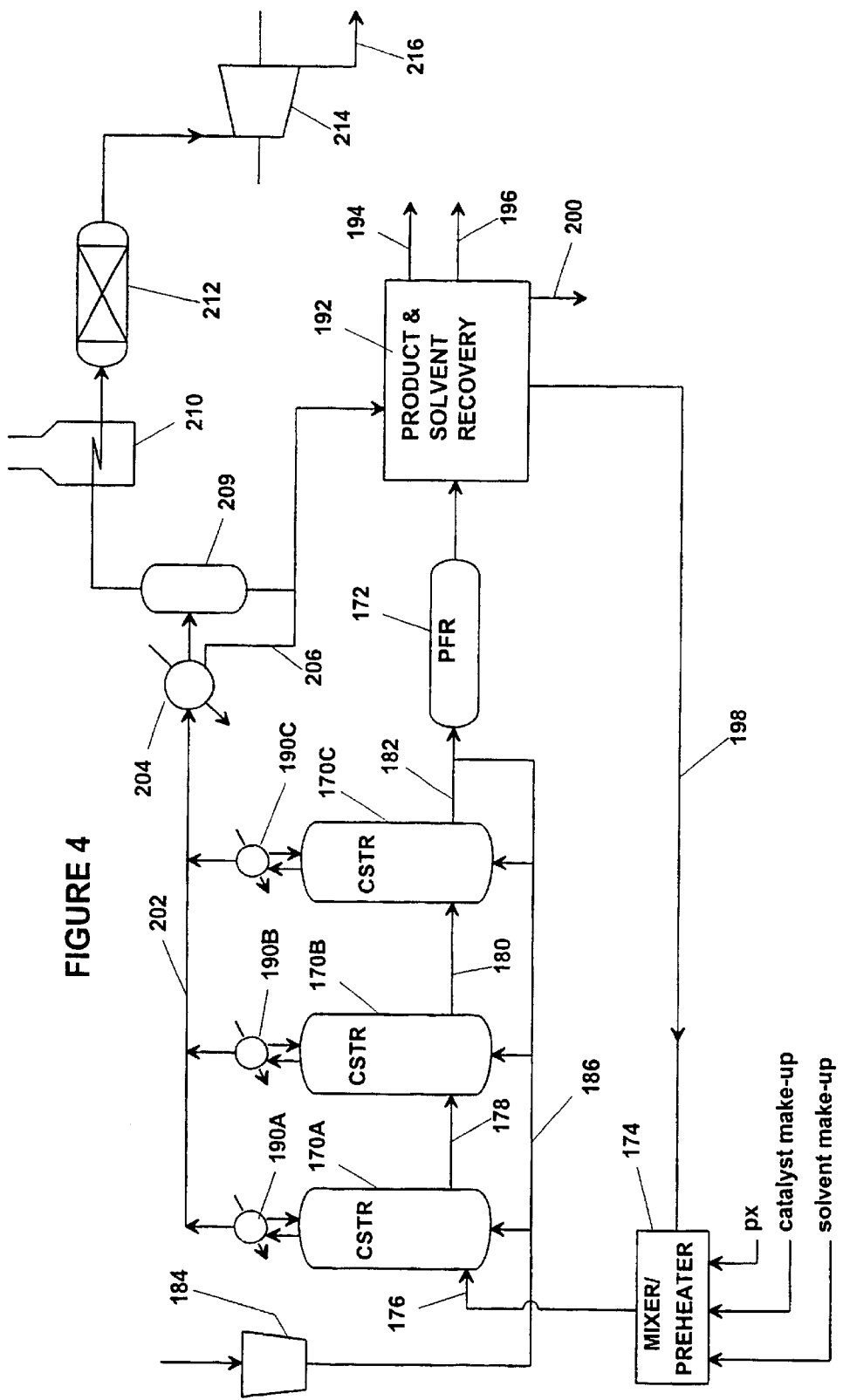
FIG. 4 is an alternative scheme in which the reaction is carried out using continuous stirred tank reactors.

In the embodiment of FIG. 2, the oxidation reaction is carried out in one ore more plug flow reactors. FIG. 4 illustrates an alternative approach in which the reaction zone is formed by a series of continuous stirred tank reactors 170A, 170B and 170C, optionally in combination with a small plug flow reactor 172. In this embodiment, plug flow-like operation is approximated by the use of multiple CSTRs—the greater the number of CSTRs employed, the closer the reactor system approaches operation in a plug flow regime and hence a more favourable burn versus 4-CBA relationship. The reaction medium from mixer/preheater 174 has the composition described with reference to the embodiment of FIG. 2 and is pressurised by pumping for supply to the inlet 176 of the reaction system, namely the inlet of the first CSTR 170A of the series, the reaction medium being pressurised to a pressure allowing sufficient margin to avoid any significant boiling thereof in each CSTR, e.g. a pressure of about 25 bara. The effluent from each CSTR is supplied to the next via lines 178 and 180 and to the plug flow reactor 172 (where present) via line 182. Air or oxygen in a diluent gas such as $CO_2$ is compressed by compressor 184 to a pressure of about 32 bara and is supplied to each CSTR via line 186 and also to the plug flow reactor 172 when present. In a modification, substantially pure oxygen may be used as the oxidant supplied to the CSTRs and/or the plug flow reactor provided that suitable precautions are taken with regard to the hazards associated with the presence of high levels of oxygen in the system. For instance, the CSTRs may be supplied with air while the plug flow reactor may be supplied with substantially pure oxygen or an enriched oxygen source such as oxygen combined with a diluent gas such as $CO_2$ or nitrogen. Regardless of the form in which the oxygen is supplied, the air/oxygen flow to each CSTR will desirably be controlled on exit oxygen to that CSTR to ensure that it does not become starved of oxygen.

In the reaction zone, the temperature of the reaction medium is engineered in such a way that substantially all of the terephthalic acid produced by oxidation of the paraxylene on that pass through the reaction zone is maintained in solution. In this context, it will be appreciated that there may be some terephthalic acid present in the solid phase in the form of undissolved fines from the mother liquor recycle as mentioned previously. Thus, in one scenario where the reaction medium supplied to the inlet region of the reaction zone is at a temperature of the order of 150° C., the first CSTR 170A may operate at a temperature of about 180° C., the second at a temperature of about 200° C. and the third at a temperature of about 210° C. thereby developing a temperature profile consistent with maintaining substantially all of the terephthalic acid formed in solution. In other words, as the reaction progresses and more terephthalic acid forms, the reaction medium is passed to the next CSTR where the temperature is sufficient to maintain in solution the terephthalic acid already formed, and that which will be formed in the CSTR concerned. The same pressure may prevail within each CSTR but we do not exclude the possibility of operating the reactor system so that the pressure is increased from one CSTR to the next.

Depleted air is removed from each CSTR 170A, B, C in an overheads stream which passes through a respective condenser 190A, B, C. These condensers are not for condensation of bulk boiloff (as in the conventional design) since the CSTRs are operated in a non-boiling regime; instead the condensers serve to "knock back" some of the solvent that may be entrained as vapour or droplets in the depleted air stream. The residence time of the reaction medium in each CSTR will be relatively short compared with the residence time, typically 30 minutes or more, in a conventional terephthalic acid-producing CSTR. Typically the residence time in each CSTR 170A, B, C may be of the order of several minutes, e.g about 1 to 2 minutes per CSTR.

The product stream withdrawn from the final CSTR 170C may be passed directly to the product/solvent recovery section 192 but where low 4-CBA terephthalic acid product is desired without excessive burn of the solvent, a small plug flow reactor 172 can be employed to further reduce the 4-CBA and other impurity content of the product exiting the final CSTR 170C. The plug flow reactor employed for this purpose need only be relatively small—for example where the CSTR's may each have a volumetric capacity of the order of 100 $m^3$, the plug flow reactor 172 may have a capacity of the order of 10 to 20 $m^3$. Thus, for example, the major part (e.g. at least 75%) of the terephthalic acid obtained in the oxidation reaction may be produced in the CSTRs with the remainder being produced in the plug flow reactor.

The product/solvent recovery section 192 will be generally similar to that described with reference to FIGS. 1 and 2. Lines 194, 196, 198 and 200 respectively depict the terephthalic acid product recovered, recovered water, mother liquor recycle to the mixer/preheater 174 and mother liquor purge. The depleted air stream from the condensers 190A, B, C will be at high pressure, e.g. 25 to 30 bara, and will contain inter alia residual oxygen, carbon monoxide, carbon dioxide, a substantial amount of nitrogen, solvent and other organics such as methyl bromide and methyl acetate. This vent gas stream 202 is further cooled in condenser 204 and the condensate, primarily solvent, is fed via line 206, to the solvent recovery section. The cooled vent gas stream is then contacted with scrubbing liquor in high pressure absorber 209 to remove further organics. The scrubbed vent gas is preheated in fuel-fired preheater 210, subjected to catalytic combustion in unit 212 and passed through expander 214 to recover power. The nitrogen-containing gas stream 216 recovered from the expander 214 may then be processed further, e.g. by scrubbing with water or alkali, to remove any residual pollutants such as bromine and/or HBr before being discharged and/or used for other duties, e.g. inerting duties, in the production plant. The vent gas treatment process may be generally as described in published International Patent Application No. WO 96/39595.

In a modification of the embodiment of FIG. 4, where the plug flow reactor is present, a single CSTR may be used instead of a series as illustrated. The arrangement may for instance be such that the major part of the oxidation reaction is conducted in the CSTR, e.g. of the terephthalic acid product obtained from the overall reaction, at least 75% is produced in the CSTR and the remainder produced in the plug flow reactor. In another modification, the or each CSTR may be supplied with substantially pure oxygen or an enriched oxygen gas (i.e. an oxygen concentration in excess of that present in air—e.g. 23 to 100%) designed in the manner disclosed in U.S. Pat. No. 5,371,283 with means for establishing a quiescent zone within the reactor in such a way that the oxygen bubbles are confined to the recirculating body of liquid and are suppressed from entering the reactor headspace. As disclosed in U.S. Pat. No. 5,371,283 (the entire disclosure of which is incorporated herein by this reference), this may be effected by means of a baffle located in the region of the interface between the gas and liquid phases and/or by flooding the headspace within the reactor with an inert gas such as nitrogen. In this manner, the oxygen content of the vent gas may be monitored relatively easily in order to avoid flammability hazards in the reactor headspace.

In those embodiments described above where one or more plug flow reactors are used, the reactor is shown orientated with its longitudinal axis extending horizontally. However, it will be appreciated that this is not essential and that the reactor may for instance be orientated so that the flow of liquid takes place in a generally vertical direction.

Figure 5:
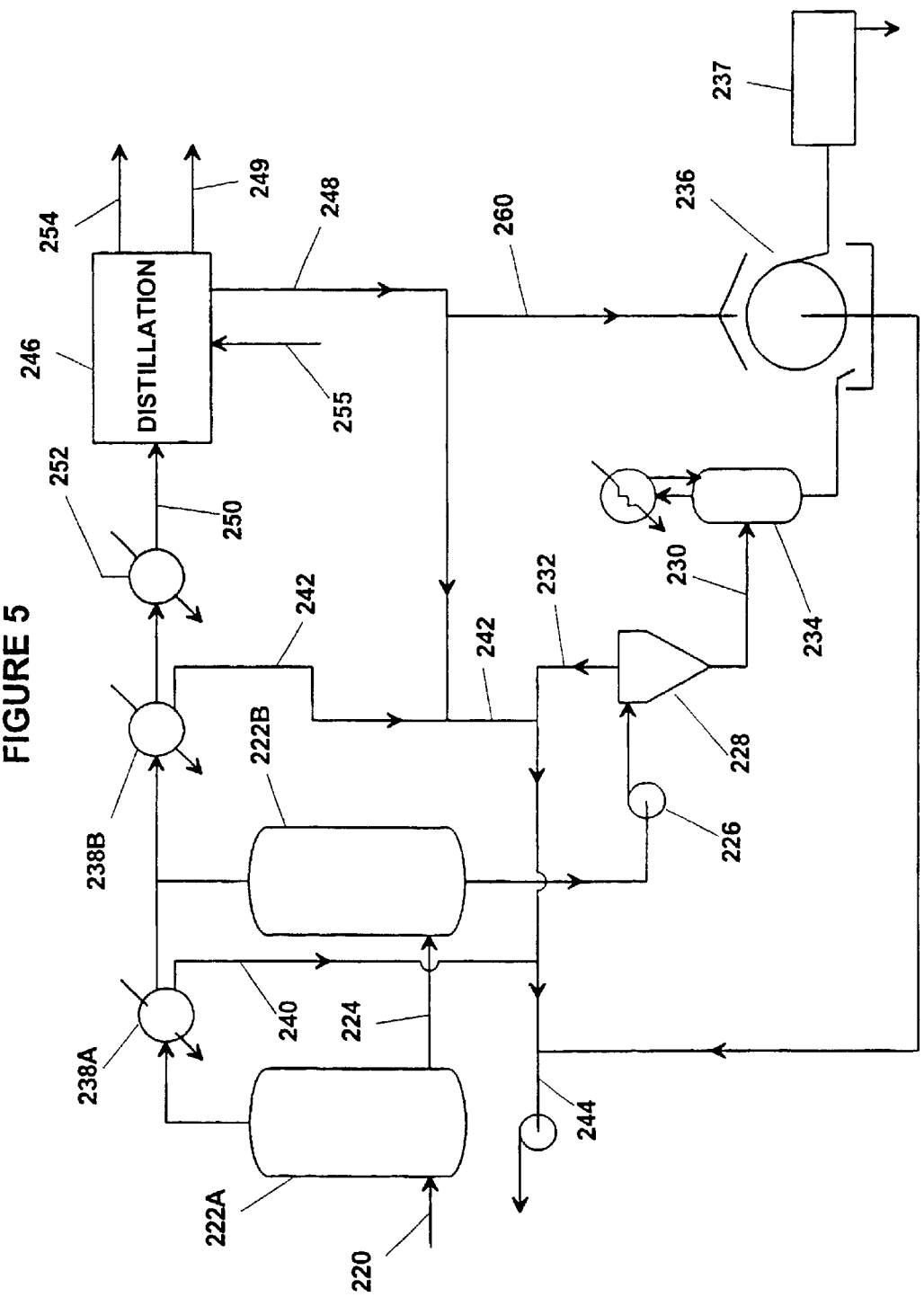
FIG. 5 is a flow sheet of one embodiment for use in the crystallisation and recovery of terephthalic acid.

One form of product recovery section as depicted in FIGS. 1, 2 and 4 is illustrated in FIG. 5 to which reference is now made. The product stream on line 220 from the reactor system enters a first stirred crystalliser vessel 222A in which it is flashed to lower pressure and temperature resulting in partial precipitation of the terephthalic acid content of the product stream and evolution of vapour comprising solvent and water. The product stream is next passed via line 224 to a second stirred crystalliser vessel 222B in which it is flashed to even lower pressure and temperature with consequent further precipitation of terephthalic acid crystals and evolution of solvent and water vapour. Typically, for a product stream on line 220 at a temperature of the order of 210 to 220° C., the product stream will be flashed to about 195° C. and 9 bara in the first crystalliser and to about 151° C. and 3 bara in the second crystalliser. Although in FIG. 5 two stages of crystallisation are illustrated, it will be appreciated that there may be more than two stages or even a single stage of crystallisation.

The product stream comprising precipitated terephthalic acid crystals in solvent-based mother liquor is in the form of a relatively thin slurry—e.g. containing about 3.5 wt % solids. This slurry is fed via pump 226 to one or more hydrocyclones 228 (only one is illustrated in FIG. 5, where more than one is employed, they will usually be parallel and/or series). The slurry undergoes thickening in the hydrocyclone(s) 228 resulting in a thickened underflow stream 230, e.g. up to about 30 wt % solids, and an overflow stream 232 comprising solvent-based mother liquor in which terephthalic acid fines are suspended. The underflow stream is supplied to a pressure letdown vessel 234 in which the pressure of the thickened slurry is reduced to approximately 1 bara or below and is fed to the slurry receiving chamber of a rotary vacuum filter 236 by means of which the terephthalic acid crystals are largely separated from mother liquor to produce a filter cake on the cylindrical filter cloth of the vacuum filter. The filter cake is removed from the filter cloth and supplied to a drier 237 to produce dried terephthalic acid crystals.

Solvent is recovered from the crystallisation process at various stages. The solvent and water-containing vapour flashed from vessels 222A, B is recovered and passed through condensers 238A, B producing solvent as condensate which is recycled via lines 240, 242 and 244 to the mixer section (see FIGS. 1, 2 and 4). Solvent is recovered as the overflow from the hydrocyclone and is recycled via line 232 and 244. Further solvent is recovered from solvent recovery section 246 and is recycled via lines 248, 242 and 244. Solvent recovery section 246 may be constituted by a distillation column (not shown), e.g. an azeotropic distillation column, to which solvent and water-bearing feedstreams arising from various sources within the production process are fed in order to separate solvent from water, the water being passed to an aqueous effluent treatment system (not shown) via line 249. One such feedstream comprises the flash vapour stream 250 obtained from the crystalliser vessels 222A, B following heat recovery in condensers 238A, B and 252. The vapour stream 250 will also contain residual oxygen and inerts such as nitrogen, carbon monoxide, carbon dioxide, solvent, water and methyl acetate (the latter being present when air is used as the source of oxygen). A second solvent/water feedstream 255 comprising solvent/water evaporated from a purge taken from the mother liquor recycle stream is supplied to the distillation column. The gaseous components are phase separated from the overheads produced in the course of distillation and are supplied via line 254 to vent gas treatment (e.g. catalytic combustion, power recovery via an expander and scrubbing). The solvent recovered from the distillation column will usually be sufficiently clean to permit its use in washing of the recovered terephthalic acid. Thus, for instance, part of the solvent stream 248 may be diverted via line 260 and used in washing of the filter cake formed on the filter cloth of the rotary vacuum filter 236. If desired, the solvent may be used for countercurrent washing of the filter cake on the filter cloth. Although a rotary vacuum filter is illustrated in FIG. 5, it will be appreciated that the solids-liquid separation step may be carried out using other devices, e.g. a belt filter. Instead of using solvent for washing, water may be used as the wash liquor.

Figure 6:
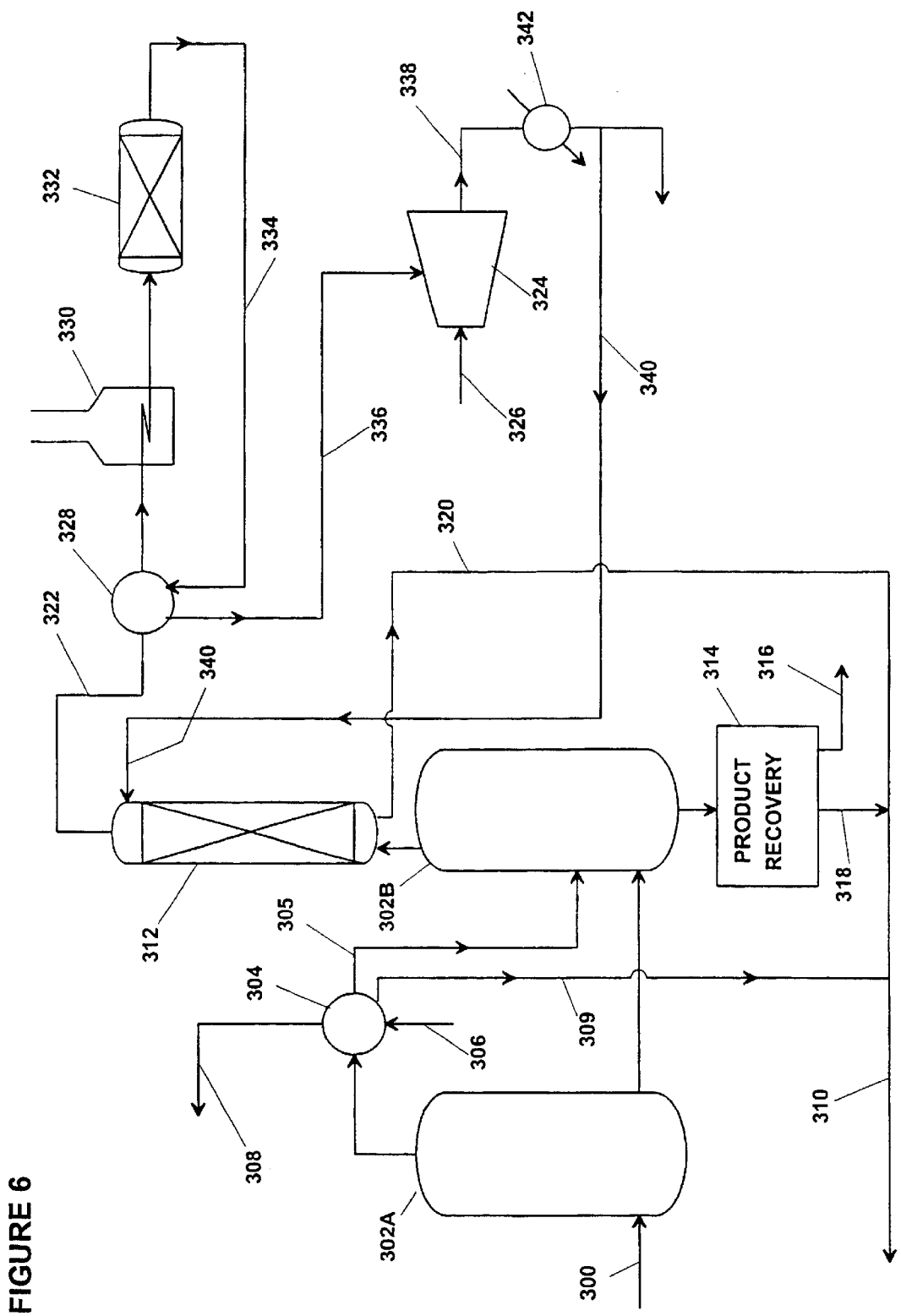
FIG. 6 is a flow sheet illustrating use of a rectifier to recover solvent and water from flash vapours produced in the crystallisation process.

FIG. 6 illustrates one form of solvent recovery from the crystallisation process in which energy is recovered by means of a condensing steam turbine. The product stream 300 from the reactor system is subjected to crystallisation, two stages being shown. The crystallisation in each vessel 302A, B takes place in the manner described with reference to FIG. 5 and results in a flash stream comprising steam and solvent vapours. The flash from vessel 302A is passed to a condenser 304 in which heat is transferred to boiler feed water supplied via line 306 thereby producing low pressure steam in line 308 for use in the production process. The condenser 304 serves to "knock back" solvent which, because it is free of terephthalic acid, is passed via line 309 to solvent recycle line 310 leading to the mixer/preheater associated within the reactor rather than being transferred into the second crystalliser vessel 302B. The uncondensed, solvent-depleted flash is passed via line 305 to the second crystalliser vessel 302B where it combines with the flash from that vessel and is passed directly to a fractional distillation/rectifier column 312. Alternatively the flash derived via line 305 can be fed directly to vent treatment as described below. The flash vapours from the vessel 302B will be at pressure, typically of the order of 3 bara. The distillation column 312 will usually be arranged to receive the flash vapours from the last crystallisation stage where a series of crystallisation stages are used; however, we do not exclude the possibility of connecting the distillation column with one of the crystallisation stages upstream of the final stage. The slurry from the vessel 302B is supplied to the solids recovery process, depicted by reference 314, producing dried terephthalic acid crystals on line 316 and mother liquor recycle on line 318.

The column 312 produces a bottoms product (line 320) comprising solvent containing a small amount of water and a water-rich overheads product (line 322) containing some solvent. The solvent-rich bottoms product is recycled to the reactor system via line 310 while the overheads product is processed to recover power by means of steam condensing turbine 324 which may receive steam on input line 326, e.g derived from line 308, and lower pressure steam derived from the overheads product (line 322). The stream of residual organics, residual oxygen, nitrogen and steam forming the overheads product on line 322 is preheated by passage through heat exchanger 328 and by fired heater 330. It is next subjected to catalytic combustion in unit 332 to destroy pollutants (mainly solvent). The resulting high pressure, high temperature stream on line 334 (typically at a temperature of the order of 450° C. following catalytic combustion) is cooled in heat exchanger 328 by heat transfer to the incoming overheads stream on line 322 so as to adjust its temperature for compatability with efficient operation of the condensing steam turbine 324 to which it is supplied via line 336, i.e. to give approximately 12% wetness at the turbine outlet 338. The outlet stream from the turbine 338 is cooled in heat exchanger 342 and may, in part, be used as reflux (line 340) in the distillation column 312. The remaining water recovered from the turbine 324 may be used elsewhere in the production process or passed to effluent treatment, e.g. as boiler feed water fed to condenser 304. In a modification of the distillation scheme of FIG. 6, all of the flash from the first crystalliser 302A may be directly letdown into the second crystalliser 302B.

Figure 7:
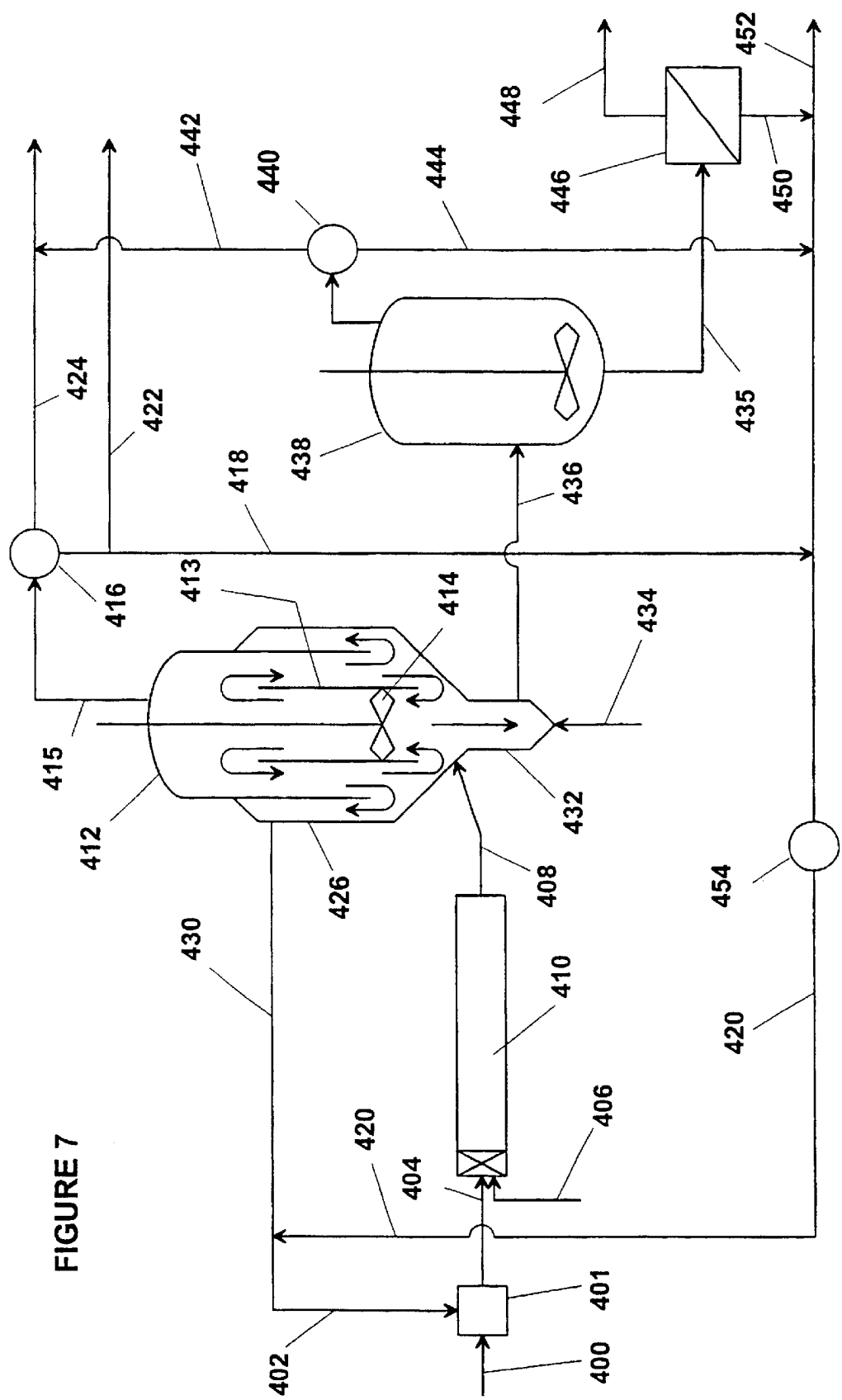
FIG. 7 is a flow sheet illustrating a product recovery scheme in which crystallisation and concentration are carried out in the same vessel.

As mentioned previously, the slurry obtained in the course of crystallisation will be thin which means that concentration of the product relative to the mother liquor content is desirable before effecting solids-liquid separation. FIG. 7 illustrates apparatus for securing concentration in the course of the crystallisation process using an integrated crystallisation and concentration apparatus. Referring to FIG. 7, the crystallisation/concentrator section comprises a Draft Tube Baffle (DTB) crystalliser. In FIG. 7, several sub-sections of plant (e.g. solvent dehydration, solids drying, purge treatment) and pumps and control valves are not shown to aid clarity of description. The omitted sub-sections of plant may be based on conventional terephthalic acid production technology.

Oxygen supplied under pressure via line 400 and hot mother liquor recycle supplied via line 402 are mixed in mixer 401 to pre-dissolve the oxygen and produce oxygenated mother liquor feed 404. At entry to plug flow reactor 410, feed 406 comprising fresh paraxylene, catalyst and acetic solvent is mixed with the oxygenated mother liquor feed 404 and reaction proceeds. The reaction exotherm results in increase in temperature through the reactor 410 and this, together with appropriate selection of the solvent-:paraxylene ratio of the reaction medium, ensures that the terephthalic acid produced is maintained in solution during the reaction. The reactor product is fed forward via line 408 to a pressure (hence temperature) controlled DTB crystalliser 412. On entering the central draft tube 413, the feed partially flashes. Because the two-phase flashing feed is less dense than the bulk mixture, a circulating flow is established within the crystalliser 412 (if necessary, the circulation is further enhanced via an up-pumping agitator 414). Vapour is disengaged from the liquor surface and passes via line 415 to a vapour condenser 416 that generates steam for process heating duties and power recovery. Most of the condensed solvent is collected for recycle with the mother liquor via lines 418, 420 and 402 but some is directed to solvent dehydration via line 422. The small gas vent stream from the condenser 416 (unreacted oxygen plus carbon oxides and low levels of volatile organics) is passed forward to a vent gas treatment process via line 424.

The DTB crystalliser 412 has a settling zone 426 from which essentially solids free mother liquor is withdrawn (it will contain some fine crystals) for recycle on line 430. Product slurry is withdrawn from an elutriation leg 432 at higher slurry strength, e.g. up to about 30% solids by weight. In the elutriation leg 432, the crystals may be washed with a countercurrent flow of clean solvent supplied via line 434. The solids-rich slurry is passed forward via line 436 for slurry cooling and depressurising, for example by means of a single flash crystalliser vessel 438 (or a number of crystallisers in series), with heat rejection via condenser 440 to cooling water and/or to heat recovery, the resulting non-condensibles being routed via line 442 and 424 to vent gas treatment and the condensate being routed via line 444 for recycle via lines 420 and 402. The cooled and depressurised slurry is then fed forward via line 435 to product separation section 446, for example a rotary or belt filter or a centrifuge, operating at super, atmospheric or sub-atmospheric pressure. Wet solid product is recovered via line 448 for product drying. Secondary mother liquor is recovered from the separation section 446 via lines 450. A small purge of mother liquor is taken via line 452 to remove soluble impurities from the process. The purge is shown as taken from the product separation liquors but could be taken, for example, from the primary mother liquor stream 430.

Solvent (and optionally catalyst) recovered from the mother liquor purge stream 452, product drying, solvent dehydration and all crystalliser condenser condensate streams are combined, pre-heated (where necessary by heater 454) and mixed with primary mother liquor recycle 430. On mixing, any fines in the primary mother liquor will tend to dissolve (a fines dissolution vessel may be provided to provide residence time for this dissolution). Fines remaining undissolved will tend to go into solution in the reactor as the solvent temperature increases.

As mentioned previously, the temperature profile through the reactor system, e.g. a single plug flow reactor, may be tailored to requirements, particularly to take into account constraints imposed by chemistry and chemical engineering considerations. For example, it will ofter be desirable for the reactor inlet temperature to be as low as possible provided that it is above the reaction initiation temperature. Advantageously, it will be at, or close to, the temperature at which the terephthalic acid is separated from the bulk of the mother liquor since cooling or heating of recycled mother liquor is expensive due to the large flows involved. Also it has been found that product quality is strongly influenced by the temperature at which solids-liquid separation is effected. These considerations imply the desirability of a reactor inlet temperature in the range 120–180° C., e.g. 140–170° C. The outlet temperature for an adiabatic (no external heating or cooling) reactor is related to the reactor inlet temperature and the solvent ratio. However, the outlet temperature is constrained by:

the need to minimise solvent and precursor burn (i.e. acetic acid and paraxylene burn to $CO/CO_2$) indicating the desirability of operating with a reactor outlet temperature below 230° C., e.g. 210° C.; and the need to ensure that substantially all of the terephthalic acid produced remains in solution by securing a suitable combination of outlet temperature and outlet solvent flow.

With an inlet temperature in the range 160–170° C. and an outlet temperature of no higher than 210° C., a simple adiabatic reactor would require a solvent:precursor ratio of greater than 100:1. This high solvent ratio incurs significant capital and operating cost penalties around the reactor, crystalliser(s), product recovery equipment and recycle systems. Such high solvent:precursor ratios can be avoided by operating the reactor system under conditions between adiabatic and isothermal by effecting removal of some of the heat of reaction, the heat so removed being used for example to raise steam for power recovery and/or process heating duties.

Figure 8:
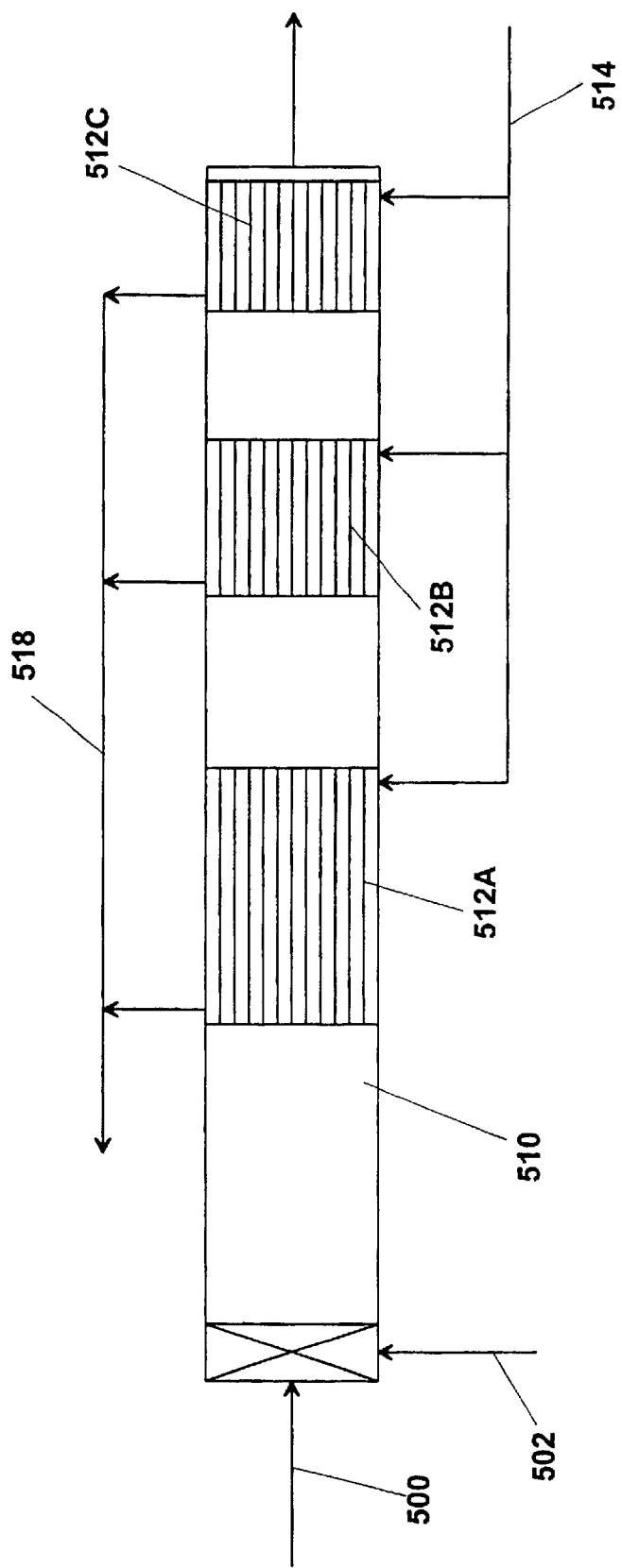
FIG. 8 illustrates one form of plug flow reactor system with provision for heat removal.

One method of removing the heat of reaction while securing a desired reactor outlet temperature is illustrated schematically in FIG. 8. In this embodiment, non-adiabatic/non-isothermal operation of the reactor system 510, supplied with reactant/solvent/recycle feeds 500, 502 is secured by internal cooling using one or more heat exchange means 512A, 512B, 512C... through which a suitable coolant, e.g. boiler feed water or mineral oil supplied by line 514, is circulated internally within the reactor system. As illustrated the heat exchangers are in the form of banks of tubes, the coolant flow being circulated through the tubes in co-current or counter-current relation with the flow of reaction medium through the reactor system. Where the coolant comprises water, the coolant may be removed as steam via line 518. The coolant used may alternatively be one of the streams employed in the process, e.g. the paraxylene feed, mother liquor recycle (before or after oxygen addition and dissolution), so that the heat recovered is employed for instance in raising the temperature of one or more of the feeds supplied to the reactor inlet. Precipitation of terephthalic acid onto the heat exchange surfaces may be avoided by suitable choice of number, size and location of cooling tubes or coils, solvent:precursor ratio, solvent operating temperatures, steam raising temperature and flow pattern. In the latter context, the coolant may flow countercurrent and/or co-current relative to the reaction medium; however, co-current flow is preferred. In FIG. 8, the reactor system may be constituted for example by a single plug flow reactor or it may comprise two or more plug flow reactors, one or more of which is provided with a heat exchanger as described above to regulate temperature.

Although the invention as described with reference to the drawings refers to using paraxylene as the terephthalic acid precursor, it will be appreciated that other precursors may be employed instead or in addition to paraxylene, e.g. 4-tolualdehyde and 4-toluic acid.

EXAMPLES

Figure 9:
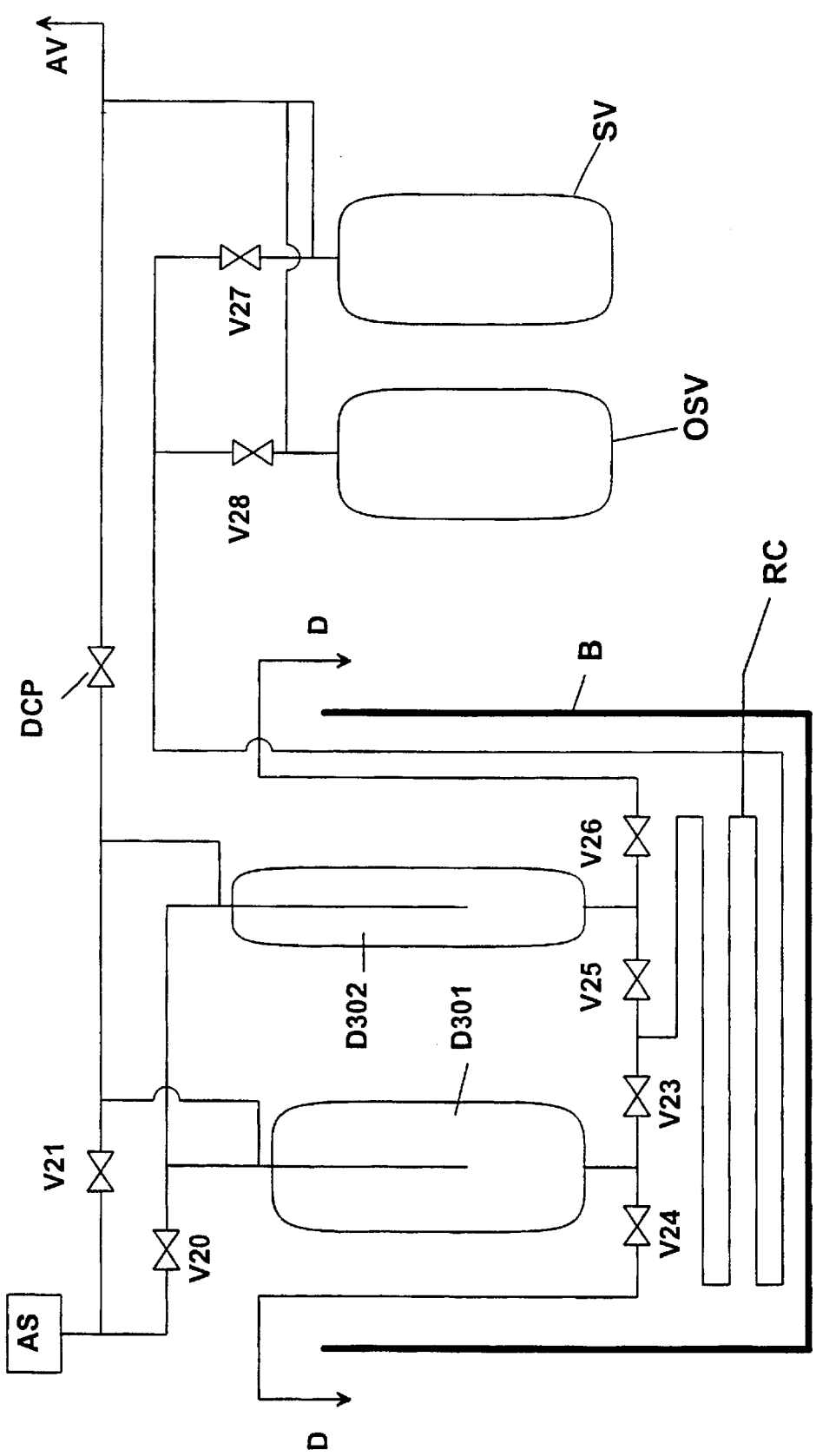
FIG. 9 is a schematic view of apparatus used in experimental work to produce the Examples reported herein.

Experimental work was carrried out using the plug flow reactor scheme illustrated in FIG. 9. Vessel D302 is charged with a known quantity of paraxylene in acetic acid/water solution. Vessel D301 is charged with a known quantity of liquid catalyst in acetic acid/water solution. Air from supply AS is introduced into both D301 and D302, through dip pipes, by opening valve V20. The system pressure is set to ensure the desired amount of oxygen (in excess of the stoichiometric paraxylene requirement) goes into solution. Following oxygen dissolution, valve V21 is opened and the differential pressure (delta P) controller DCP is set to establish a constant pressure between D301/D302 and the downstream vessels. The fixed differential pressure fixes the reactor residence time when liquid flow is established later.

Valves V23 and V25 are opened to cross-connect the two feed vessels D301 and D302. Valves V27 and V28 are kept closed, preventing flow through the plug flow reactor in the form of Reaction Coil RC which is initially filled with acetic acid. The vessels D301 and D302 and Reaction Coil are all immersed in an oil bath B which preheats the contents of vessels D301 and D302 to the required reaction temperature. When D301/D302 are at temperature, reaction is started by opening valve V28 to establish flow through the Reaction Coil into an Off-Spec Vessel OSV and consequent displacement of acetic acid from the Reaction Coil into the Off-Spec Vessel OSV. After a predetermined time, the product stream from the Reaction Coil is switched to the Sample Vessel SV by opening valve V27 and closing valve V28. Subsequently, the product stream from the Reaction Coil RC is switched back to the Off-Spec Vessel OSV. At the end of the experiment, all vessels are cooled, vented via line AV, washed out and drained via drain lines D. The solid and liquid contents of the Sample Vessel are recovered, weighed and analysed and the composition of the reaction solution leaving the Reaction Coil is back-calculated.

In Table 1, the concentrations of the reaction intermediates, paratolualdehyde (ptolald), paratoluic acid (ptol) and 4-carboxybenzaldehyde (4-CBA) are reported for experiments where the reaction residence time was varied. At the small equipment scale used, the reactions run under quasi-isothermal conditions, close to the oil bath temperature of 210° C. throughout. The Examples clearly demonstrate the effect of residence time on intermediates concentrations. At 4.86 minutes residence time, the paraxylene to reaction intermediates single pass conversion is less than 0.5%. At 1.28 minutes residence time, the paraxylene to reaction intermediates single pass conversion is about 16%. Significantly, however, paraxylene conversion to 4-CBA (the intermediate that tends to co-precipitate with the product, terephthalic acid) is of the order of 1% or below throughout.

TABLE 1

Plug Flow Reactor-Oxidation Results

In all experiments the following parameters were fixed (all compositions are w/w);

| | |
|---|---|
| Solvent | water 5%, acetic acid 95% |
| Paraxylene | 0.5% w/w (200:1 solvent ratio) |
| Catalyst | Co 632 ppm, Mn 632 ppm, Br 1264 ppm + Zr 96 ppm |
| Oil Bath Temperature | 210° C. |

| Ex | Residence Time (min) | ptolald in solution (ppm w/w) | ptol in solution (ppm w/w) | 4CBA in solution (ppm w/w) |
|---|---|---|---|---|
| 1 | 1.28 | 228 | 687 | 76 |
| 2 | 1.78 | 55 | 411 | 51 |
| 3 | 2.28 | 132 | 312 | 42 |
| 4 | 2.31 | 99 | 192 | 38 |
| 5 | 3.29 | 15 | 82 | 6 |
| 6 | 4.86 | 1.7 | 27 | <0.1 |

2. Crystallisation/Hot Filtration Experiments

A solution of 2% w/w terephthalic acid (TA), 125 ppm 4-CBA, 175 ppm ptol and other oxidation intermediates in 5% w/w water, 95% w/w acetic acid solvent is prepared at elevated temperature (210° C.) and at a pressure to maintain a liquid phase. The solution is passed, continuously, through a pressure reducing valve into a crystalliser vessel whose pressure and temperature is controlled such that the TA is precipitated from solution. The slurry produced in the crystalliser is passed forward to further crystallisation vessels in which the pressure and temperature are reduced to ambient conditions and further TA is precipitated.

During the course of the experiment, crystals from the first crystalliser (Hot Filtered TA) are recovered and are analysed for 4-CBA and paratoluic acid (ptol) content and median particle size (using a Coulter LS230 Laser Diffraction psd analyser). Crystals from the downstream vessels (Cold Filtered TA) are also recovered and analysed for reference purposes.

In Table 2, the Hot Filtered TA/4-CBA contents and median particle sizes are reported for experiments where the first crystalliser temperature, residence time and stirrer speed were varied. For reference, one analysis of Cold Filtered TA is also included. Examples 7, 8 and 9 show that, in the Hot Filtered TA, 4-CBA and ptol contents fall as the filtration temperature is reduced from 196 to 148° C. The data also shows that median particle size increases with reducing temperature. In a separate experiment, Examples 10 and 11 show that, in the Hot Filtered TA, reduction in filtration temperature from 151 to 126° C. causes 4CBA level to increase, while ptol level and median particle size reduce.

When viewed together, Examples 7 through 11 indicate an optimum first crystalliser temperature, with respect to both intermediates incorporation and median particle size, in the region 150+/−25° C., especially 140 to 170° C.

Examples 12 and 13 show that increasing first crystalliser residence time from 9 to 18 minutes benefits both intermediates incorporation and median particle size. Examples 14 and 15, when viewed alongside Example 10, show that increasing first crystalliser agitator speed, from 270 to 1000 rpm, does not have a strong influence on median particle size but reduces intermediates incorporation.

TABLE 2

Crystallisation/Hot Filtration Results
in all experiments the following parameters were fixed (all compositions are w/w);
Solvent water 5%, acetic acid 95%
Feed Solution Aromatics TA 2%, 4CBA 125 ppm, ptol 175 ppm
Feed Solution Temperature 210° C.

| Ex | First Cryst. Res. Time (min) | First Cryst. Stirrer Speed (rpm) | First Cryst. Temp (° C.) | 4CBA Content (ppm) | ptol Content (ppm) | Median Particle Size (micron) |
|---|---|---|---|---|---|---|
| 7 | 12 | 1,000 | 196 | 2,360 | 345 | 59 |
| 8 | 12 | 1,000 | 176 | 1,040 | 218 | 114 |
| 9 | 12 | 1,000 | 148 | 670 | 89 | 134 |
| 10 | 18 | 1,500 | 151 | 710 | 138 | 96 |
| 11 | 18 | 1,500 | 126 | 1,060 | 117 | 86 |
| 12 | 18 | 1,000 | 173 | 980 | 150 | 106 |
| 13 | 9 | 1,000 | 179 | 1,140 | 217 | 96 |
| 14 | 12 | 270 | 152 | 930 | 123 | 139 |
| 15 | 12 | 500 | 150 | 790 | 106 | 135 |
| Ref. | 12 | 1,000 | 148 | 2,340 (Cold Filter) | 281 (Cold Filter) | 102 (Cold Filter) |

What is claimed is:

1. A process for the production of terephthalic acid by the catalytic liquid phase oxidation of a precursor of terephthalic acid with oxygen in a reaction medium containing the precursor and an aliphatic monocarboxylic acid solvent at a solvent:precursor ratio of at least 30:1 which process comprises introducing the reactants into a reaction zone which comprises at least one continuously stirred tank reactor in series with at least one plug flow reactor under conditions of temperature and pressure whereby a continuous plug flow reaction regime is maintained and substantially all of the terephthalic acid produced in the oxidation reaction remains in solution during the reaction.

2. A process as claimed in claim 1 in which the oxidation reaction is carried out with substantially all of the oxygen dissolved in the reaction medium.

3. A process as claimed in claim 2 in which the reaction medium is produced by combining at least two separate liquid phase components and at least part of the oxygen is added to and dissolved in one or more of said liquid phase components before such components are combined to form the reaction medium.

4. A process as claimed in claim 2 or 3 in which oxygen is added to and dissolved in a mother liquor recycle stream recovered from the reaction medium following completion of the reaction.

5. A process as claim in claim 4 in which the oxygen is introduced into the reaction in the form of molecular oxygen, as air or in an oxygen-containing gas.

* * * * *